US010724071B2

(12) United States Patent
Wakabayashi et al.

(10) Patent No.: US 10,724,071 B2
(45) Date of Patent: Jul. 28, 2020

(54) METHOD FOR DETERMINING DRUG-SENSITIVE HUMAN CELL LINES BY ANALYSIS METHOD IN WHICH MEASUREMENT OF ACTIVITY OF TWO TYPES OF PROTEIN KINASE IS USED

(71) Applicant: NITTO BOSEKI CO., LTD., Fukushima-shi, Fukushima (JP)

(72) Inventors: Masayuki Wakabayashi, Koriyama (JP); Natsuki Sato, Tokyo (JP); Hideki Ishihara, Tokyo (JP)

(73) Assignee: NITTO BOSEKI CO., LTD., Fukushima-Shi, Fukushima (JP)

( * ) Notice: Subject to any disclaimer, the term of this patent is extended or adjusted under 35 U.S.C. 154(b) by 0 days.

(21) Appl. No.: 15/765,799

(22) PCT Filed: Oct. 14, 2016

(86) PCT No.: PCT/JP2016/080544
§ 371 (c)(1),
(2) Date: Apr. 4, 2018

(87) PCT Pub. No.: WO2017/065277
PCT Pub. Date: Apr. 20, 2017

(65) Prior Publication Data
US 2018/0291421 A1 Oct. 11, 2018

(30) Foreign Application Priority Data

Oct. 14, 2015 (JP) .................................. 2015-202960

(51) Int. Cl.
*C12Q 1/32* (2006.01)
*C12Q 1/04* (2006.01)
*A61P 35/00* (2006.01)
*A61K 31/366* (2006.01)
*A61K 31/519* (2006.01)
*G01N 33/574* (2006.01)
*C12Q 1/48* (2006.01)
*G01N 33/53* (2006.01)

(52) U.S. Cl.
CPC .............. *C12Q 1/32* (2013.01); *A61K 31/366* (2013.01); *A61K 31/519* (2013.01); *A61P 35/00* (2018.01); *C12Q 1/04* (2013.01); *C12Q 1/48* (2013.01); *G01N 33/53* (2013.01); *G01N 33/574* (2013.01); *G01N 2333/91205* (2013.01); *G01N 2333/91215* (2013.01)

(58) Field of Classification Search
None
See application file for complete search history.

(56) References Cited

U.S. PATENT DOCUMENTS

| 2010/0167945 A1 | 7/2010 | Singh et al. |
| 2013/0012407 A1 | 1/2013 | Liu et al. |
| 2014/0273006 A1 | 9/2014 | Singh et al. |
| 2015/0031882 A1 | 1/2015 | Hsu et al. |

FOREIGN PATENT DOCUMENTS

| JP | 2007-503809 A | 3/2007 |
| JP | 2009-050183 A | 3/2009 |
| JP | 2010-507384 A | 3/2010 |
| JP | 2010-536371 A | 12/2010 |
| JP | 2011-514522 A | 5/2011 |
| JP | 2013-517461 A | 5/2013 |
| JP | 2013-174616 A | 9/2013 |
| JP | 2015-505959 A | 2/2015 |
| JP | 2015-515476 A | 5/2015 |

OTHER PUBLICATIONS

Chappell, W. et al., "Ras/Raf/MEK/ERK and PI3K/PTEN/Akt/mTOR Inhibitors: Rationale and Importance to Inhibiting These Pathways in Human Health", *Oncotarget*, vol. 2, No. 3, 2011, pp. 135-164.
Dreaden, E. et al., "Tumor-Targeted Synergistic Blockade of MAPK and PI3K from a Layer-by-Layer Nanoparticle", *Clin. Cancer Res.*, vol. 21, No. 19, Oct. 1, 2015, pp. 4410-4419.
"Guideline for Treatment of Breast Cancer Based on Scientific Basis 1", *Japanese Breast Cancer Society*, 2015, 10 pages (including English Machine Translation).
Harris, L. et al., "American Society of Clinical Oncology 2007 Update of Recommendations for the Use of Tumor Markers in Breast Cancer", *Journal of Clinical Oncology*, vol. 25, No. 33, Nov. 20, 2007, pp. 5287-5312.
Jing, J. et al., "Comprehensive Predictive Biomarker Analysis for MEK Inhibitor GSK1120212", *Molecular Cancer Therapeutics*, vol. 11, No. 3, Mar. 2012, pp. 720-729.
Klammer, M. et al., "Phosphosignature Predicts Dasatinib Response in Non-Small Cell Lung Cancer", *Molecular & Cellular Proteomics*, 11.9, 2012, pp. 651-668.
Lecture, "Abstract 2P1118", *Biochemistry and Molecular Biology*, 2015, 4 pages (with English language translation).
Lecture, "Abstract 2P1129", *Biochemistry and Molecular Biology*, 2015, 4 pages (with English language translation).
Lehmann, B. et al., "Identification of Human Triple-Negative Breast Cancer Subtypes and Preclinical Models for Selection of Targeted Therapies", *Journal of Clinical Investigation*, vol. 121, No. 7, Jul. 2011, pp. 2750-2767.
Leung, E. et al., "Relationships Between Signaling Pathway Usage and Sensitivity to a Pathway Inhibitor: Examination of Trametinib Responses in Cultured Breast Cancer Lines", *PLOS One*, vol. 9, No. 8, Aug. 2014, pp. 1-12.

(Continued)

*Primary Examiner* — Brian J Davis
(74) *Attorney, Agent, or Firm* — Brinks Gilson & Lione

(57) ABSTRACT

The present invention addresses the problem of providing a novel method for classifying cancer cells by an analysis method in which measurement of the activity of two types of protein kinase is used. Cancer cells are newly classified and drug sensitivity is predicted on the basis of the ratio of the activity of two types of protein kinase derived from the same sample.

12 Claims, 37 Drawing Sheets

(56) References Cited

OTHER PUBLICATIONS

Sato, N.et al., "Abstract P5-02-06: Predicting the Response of Molecular Targeting Agents in Triple-Negative Breast Cancer Cell Lines by Kinase Activities", *Cancer Research*, vol. 76, No. 4, 2016, 2 pages.
Tomao, F. et al., "Triple-Negative Breast Cancer: New Perspectives for Targeted Therapies", *OncoTargets and Therapy*, vol. 8, 2015, pp. 177-193.
Toss, A. et al., "Molecular Characterization and Targeted Therapeutic Approaches in Breast Cancer", *Breast Cancer Research*, vol. 17, No. 60, 2015, 11 pages.
Yuen, H.F. et al., "Impact of Oncogenic Driver Mutations on Feedback Between the PI3K and MEK Pathways in Cancer Cells", *Bioscience Reports*, vol. 32, 2012, pp. 413-422.
International Search Report, and English language translation thereof, in corresponding International Application No. PCT/JP2016/080544, dated Jan. 10, 2017, 5 pages.

GRID ANALYSIS IN WHICH PARAMETERS OF 1) ARE REPLACED WITH EXPRESSION LEVEL OF PHOSPHORYLATED SUBSTRATE (COMPARATIVE EXAMPLE 6)

GRID ANALYSIS IN WHICH PARAMETERS OF 3) ARE REPLACED
WITH EXPRESSION LEVEL OF PHOSPHORYLATION
(COMPARATIVE EXAMPLE 11)

GRID ANALYSIS IN WHICH PARAMETERS OF 4) ARE REPLACED WITH
EXPRESSION LEVEL OF PHOSPHORYLATION
(COMPARATIVE EXAMPLE 14)

GRID ANALYSIS IN WHICH PARAMETERS OF 5) ARE REPLACED WITH
EXPRESSION LEVEL OF PHOSPHORYLATED SUBSTRATE
(COMPARATIVE EXAMPLE 18)

METHOD FOR DETERMINING DRUG-SENSITIVE HUMAN CELL LINES BY ANALYSIS METHOD IN WHICH MEASUREMENT OF ACTIVITY OF TWO TYPES OF PROTEIN KINASE IS USED

This application is a 371 application of PCT/JP2016/080544 having an international filing date of Oct. 14, 2016, which claims priority to JP2015-202960 filed Oct. 14, 2015, the entire content of each of which is incorporated herein by reference.

TECHNICAL FIELD

The present invention relates to a novel method for classifying cancer cells into subtypes by an analysis method using the activity measurement of two types of protein kinase, and a method for determining the drug sensitivity of cancer cells based on the subtype classification method. The present invention further includes a method for determining the effect of a drug on a living body based on the activity measurement of protein kinases in cells derived from the living body.

BACKGROUND ART

Solid cancers (malignant tumors) are named e.g. "breast" cancer and "large intestine" cancer depending on the sites of onset and metastasis; however, cancer cells, the cause of a disease, are various. Cancers in one tissue are variously classified with the development of molecular biology, and correlation with the effect of an anticancer drug has been studied.

Breast cancer is a cancer in which mammary gland lobular epithelium secreting milk, or mammary duct epithelium which is a passage to mammary duct becomes malignant, and is the most frequent malignant tumor among Japanese women in recent years. Various genes including BRCA1 and BRCA2 are suggested to be involved in breast cancer, and classified into various subtypes by their expression levels.

There are, for example, classification by the expression levels of estrogen receptor (ER) and progesterone receptor (PgR) related to the estrogen dependency of cancer cell growth, and classification by the expression level of Human EGFR-Related2 (HER2), a receptor tyrosine kinase which is also a cancer gene.

Antiestrogen drugs (such as tamoxifen) are effective for cancers in which the expression levels of estrogen receptor (ER) and progesterone receptor (PgR) are higher, and trastuzumab, an anti-HER2 monoclonal antibody, for example is effective for cancers in which the expression of HER2 is higher, and they are administered to patients.

Accordingly, breast cancer has a good pathological complete response (pCR) rate when the expression levels of estrogen receptor (ER) and progesterone receptor (PgR) are higher and the expression of HER2 is higher. That is, the pCR rate is better in 1: (ER·PgR-positive, HER2-positive)=(sensitive to antiestrogen drugs, sensitive to anti-HER2 monoclonal antibodies) (luminal B (HER2-positive) type), 2: (ER·PgR-positive, HER2-negative)=(sensitive to antiestrogen drugs, insensitive to anti-HER2 monoclonal antibodies) (luminal A type or luminal B (HER2-negative) type), or 3: (ER·PgR-negative, HER2-positive)=(insensitive to antiestrogen drugs, sensitive to anti-HER2 monoclonal antibodies) (non-luminal type).

HER2 and ER are called predictive factors because of a relation to the effect of therapy, and are clinically applied (Non-patent Literature 10). A factor whose presence or absence is correlated with prognosis is called a prognostic factor. PgR is currently thought to be a prognostic factor. It is often to use mainly an immunohistochemical method (IHC method) for tumor tissue samples to detect a predictive factor. Either a method in which both the staining intensity of tumor cells and the ratio of stained cells are considered (such as AllredScore) or a method in which the staining intensity is not evaluated and only the ratio of stained tumor cells is used for determination (such as J-Score) is used.

HER2 is generally diagnosed by an IHC method, and determined as negative when the result is 0 or 1+, and as positive for 3+. When the result is 2+, the presence or absence of amplification is examined by a FISH method (Fluorescence in situ hybridization), and HER2 is determined as positive when there is amplification and as negative when there is not amplification.

ER is determined as positive when AllredScore is 3 to 8, and it is often to set 10% as a cutoff value when determining ER by the ratio of stained cells; however, there is also an opinion that when the cells are present even at 1%, ER should be determined as positive. In any case, when a fixed cutoff value is set and these genes (predictive factors) are determined as positive, these can be effective guidelines for therapy regimens.

However, it is reported that there is triple negative breast cancer (TNBC) (ER-negative, PgR-negative, HER2-negative), in which the expression of all the ER, PgR and HER2 is not observed and to which the above antiestrogen drugs and HER2 monoclonal antibody are not effective as an anticancer drug, in breast cancers.

Triple negative breast cancer (TNBC) is present at 11 to 23% in all breast cancers, and is currently thought to have poor prognosis. The effects of not only the above target-specific drugs but also other general anticancer drugs vary depending on patients, and it is suggested to require further subtyping (Non-patent Literatures 7 and 8).

It is shown that TNBC can be currently classified by gene profiles into at least the following 6 subtypes in academics:

Two basal-like (BL1 and BL2) subtypes (with high expression of cell cycle-related genes and DNA damage response genes);

Immunomodulatory (IM) subtype (with high expression of genes related to immune reactions);

Mesenchymal (M) subtype (with high expression of genes related to TGF-β and Wnt/β-catenin signaling);

Mesenchymal-stem like (MSL) subtype (with expression of M type+high expression of stem cell-related genes); and Luminal androgen receptor (LAR) subtype (with high expression of AR and luminal-related genes).

However, it is difficult to correlate such gene expression profiles with the drug sensitivity of cancer cells, and basic studies have been still advanced (Patent Literatures 1, 2 and 3; Non-patent Literatures 1, 2 and 9).

CITATION LIST

Patent Literature

PATENT LITERATURE 1: JP-A-2009-050183
PATENT LITERATURE 2: JP-A-2013-174616
PATENT LITERATURE 3: JP-A-2007-503809

PATENT LITERATURE 4: JP-A-2010-507384
PATENT LITERATURE 5: JP-A-2010-536371
PATENT LITERATURE 6: JP-A-2015-505959

Non-Patent Literature

NON-PATENT LITERATURE 1: Harris L1, Fritsche H, Mennel R, Norton L, Ravdin P, Taube S, Somerfield M R, Hayes D F, Bast R C Jr, American Society of Clinical Oncology 2007 update of recommendations for the use of tumor markers in breast cancer. J Clin Oncol. 2007 Nov. 20; 25(33):5287-312. Epub 2007 Oct. 22.

NON-PATENT LITERATURE 2: Leung E Y, Kim J E, Askarian-Amiri M, Rewcastle G W, Finlay G J, Baguley B C. Relationships between signaling pathway usage and sensitivity to a pathway inhibitor: examination of trametinib responses in cultured breast cancer lines. PLoS One. 2014 Aug. 29; 9(8):e105792.

NON-PATENT LITERATURE 3: Chappell W H, Steelman L S, Long J M, Kempf R C, Abrams S L, Franklin R A, Bäsecke J, Stivala F, Donia M, Fagone P, Malaponte G, Mazzarino M C, Nicoletti F, Libra M, Maksimovic-Ivanic D, Mijatovic S, Montalto G, Cervello M, Laidler P, Milella M, Tafuri A, Bonati A, Evangelisti C, Cocco L, Martelli A M, McCubrey J A. Ras/Raf/MEK/ERK and PI3K/PTEN/Akt/mTOR inhibitors: rationale and importance to inhibiting these pathways in human health. Oncotarget. 2011 March; 2(3):135-64.

NON-PATENT LITERATURE 4: Yuen HF1, Abramczyk O, Montgomery G, Chan K K, Huang Y H, Sasazuki T, Shirasawa S, Gopesh S, Chan K W, Fennell D, Janne P, El-Tanani M, Murray J T. Impact of oncogenic driver mutations on feedback between the PI3K and MEK pathways in cancer cells. Biosci Rep. 2012 August; 32(4): 413-22.

NON-PATENT LITERATURE 5: Jing J, Greshock J, Holbrook J D, Gilmartin A, Zhang X, McNeil E, Conway T, Moy C, Laquerre S, Bachman K, Wooster R, Degenhardt Y. Comprehensive predictive biomarker analysis for MEK inhibitor GSK1120212. Mol Cancer Ther. 2012 March; 11(3):720-9.

NON-PATENT LITERATURE 6: Klammer M, Kaminski M, Zedler A, Oppermann F, Blencke S, Marx S, Müller S, Tebbe A, Godl K, Schaab C Phosphosignature predicts dasatinib response in non-small cell lung cancer. Mol Cell Proteomics. 2012 September; 11(9):651-68, NON-PATENT LITERATURE 7: Lehmann B D, Bauer J A, Chen X, et al.: Identification of human triple-negative breast cancer subtypes and preclinical models for selection of targeted therapies. J Clin Invest 121: 2750-2767, 2011.

NON-PATENT LITERATURE 8: Toss A, Cristofanilli M. Molecular characterization and targeted therapeutic approaches in breast cancer. Breast Cancer Res. 2015 Apr. 23; 17(1):60.

NON-PATENT LITERATURE 9: Tomao F, Papa A, Zaccarelli E, Rossi L, Caruso D, Minozzi M, Vici P, Frati L, Tomao S. Triple-negative breast cancer: new perspectives for targeted therapies. Onco Targets Ther. 2015 Jan. 16; 8:177-93. doi: 10.2147/OTT.S67673. eCollection 2015. Review.

NON-PATENT LITERATURE 10: GUIDELINE FOR TREATMENT OF BREAST CANCER BASED ON SCIENTIFIC BASIS 1, Treatment (Japanese Breast Cancer Society)

SUMMARY OF INVENTION

Technical Problem

The inventors of the application have also studied that a dosing guideline for anticancer drugs can be decided by profiling cancer cells, and hypothesized that classification into subtypes was possible not by a plurality of gene expression profiles but by a plurality of signal cascades.

Based on the hypothesis, the inventors of the application searched whether cancer cells can be classified by a plurality of various cascades. However, a significant correlation could not be obtained in classification based on the expression levels of existing genes as shown in Comparative Examples in the Description of the application.

However, the inventors of the application have believed their own hypothesis, moreover have diligently studied and have proved their own hypothesis by means described below.

Accordingly, a problem to be solved in the invention of the application is to prove the above hypothesis, and more specifically to provide a novel method for classifying cancer cells into subtypes, and a method for determining the drug resistance of cancer cells based on the subtype classification method. Such method can determine the drug sensitivity of the cancer cells, for example, using cancer tissue cells isolated from a cancer patient, and can be applied to use the result for the drug therapy of the patient etc.

Solution to Problem

The inventors of the application repeated diligent studies and various trial and error (see Comparative Examples). Methods for measuring indirect factors such as the expression levels, expression patterns and mutational patterns of related genes described above, and the phosphorylation patterns and phosphorylation levels of molecules contained in signal transduction pathways etc. have been tried; however, a significant correlation could not be obtained in all the methods, and a correlation between signal cascade and drug resistance could be obtained only in an aspect below.

That is, the present invention is a method for classifying cancer cells into four subtypes (sensitive to a PI3K inhibitor and sensitive to an MEK inhibitor), (sensitive to a PI3K inhibitor and insensitive to an MEK inhibitor), (insensitive to a PI3K inhibitor and sensitive to an MEK inhibitor), and (insensitive to a PI3K inhibitor and insensitive to an MEK inhibitor) by directly measuring the enzyme activity of MEK and PI3K, kinases responsible for two types of primary signal transduction pathway related to the survival and growth of cancer, or further using normalization factors (e.g. the total amount of protein reflecting the number of cells and the expression level of intracellular protein which is not influenced regardless of the presence of an inhibitor).

Kinase is the generic name of enzymes which transfer a phosphate group from a molecule having a high-energy phosphate bond such as ATP to a target molecule (phosphorylate) (enzyme number: EC 2.7.1 to EC 2.7.4), and phosphatase is the generic name of enzymes which hydrolyze the target molecule to dissociate a phosphate group.

Phosphorylation normally occurs at protein residues, serine, threonine and tyrosine in eukaryotes, and kinases are classified into mainly serine/threonine kinases and tyrosine kinases depending on the targets thereof.

Kinases themselves are cell membrane receptors and target molecules of other kinases, and thus form a complicated signal network in cells.

For example, tyrosine kinases (or Protein Tyrosine Kinases; PTK, EC 2.7.10.) are involved in signal transduction related to cell differentiation, growth and adhesion or immune reactions, and roughly classified into two types, a receptor type which is activated by binding of a growth factor and a non-receptor type to which a growth factor is not bound. When being activated, a tyrosine kinase specifically phosphorylates a receptor itself or a target protein. By autophosphorylation of the receptor, various signaling transduction factors recognizing this phosphorylated site are bound to the receptor to initiate signal transduction. Also, by the phosphorylation of the target protein, various intracellular proteins are successively activated to initiate signal transduction. It is reported that there are more than 100 types of human tyrosine kinase and it is reported that they are excessively activated in cancers, atherosclerosis and psoriasis, etc.

"PI3K" (Phosphoinositide 3-kinase; EC 2.7.1.137) is an enzyme which phosphorylates the hydroxyl group at position 3 of inositol in an inositol phospholipid, a structural component of cell membrane.

EC numbers (Enzyme Commission numbers) are those which are represented with 4 sets of numbers following EC in accordance with reaction forms to organize enzymes, and are provided by Enzyme Committee in International Union of Biochemistry (currently NC-IUBMB). The definition of PI3K, for example, is described in: http://www.chem.qmul.ac.uk/iubmb/enzyme/EC2/7/1/137.html.

PI3K is classified into Class I, II and III depending on structures.

Class I PI3K is a heterodimer and is further classified into Class IA and Class IB by amino acid sequence homologies. Class IA includes p110α, β and δ, which are bound to p85α, p55α, p50α, p85β and p55γ, regulatory subunits. p85α, p55α and p50α are splicing variants of an identical gene (Pik3r1), and p85β and p55γ are derived from Pik3r2 and Pik3r3 genes, respectively. Class IA is involved in the activation of protein kinase-B (PKB) (Akt (v-Akt Murine Thymoma Viral Oncogene) of serine threonine kinase). The expression of p110γ, Class IB PI3K, is observed only in mammals, and the function thereof is regulated by G protein fry subunit and p101. PI3 kinase in Class IB is mainly activated by stimulation from G-protein-coupled receptors (GPCR), and PtdIns(3,4,5)P3 produced by the phosphorylation of PtdIns(3,4)P2 functions as a second messenger in an intracellular signal transduction mechanism.

Class II includes three isoforms, α, β and γ, and all the isoforms do not have a regulatory subunit and show an enzyme activity as a monomer.

Class III PI3K produces PtdIns(3)P from PtdIns and is functionally close to Class II, but is structurally more similar to Class I and forms a heterodimer to function. Class III PI3K is involved in e.g. the trafficking of proteins.

Examples of "PI3K inhibitors" include, but not limited to, Wortmannin ($C_{23}H_{24}O_8$=428.44 CAS No. 19545-26-7)

[Chemical Formula 1]

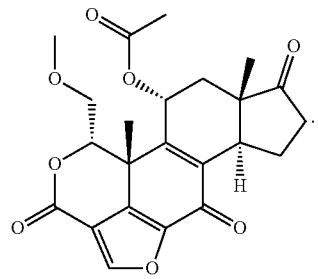

and LY294002, AS605240 and ZSTK474, and IC486068 and IC87114 which are PI3Kδ specific inhibitors.

MEK means MAP kinase-ERK kinase Kinase or mitogen-activated protein (MAP) Kinase Kinase (MAPKK), and is an enzyme which causes the phosphorylation of threonine and serine residues, which is essential to activate MAP kinase (EC 2.7.12.2).

MEK1 and MEK2; MEK4 and MEK7; MEK3 and MEK6; and MEK5 are involved in the activation of ERK1/2, the activation of JNK subfamily, the activation of p38 subfamily, and the activation of ERK5 subfamily, respectively.

Examples of "MEK inhibitors" include, but not limited to, trametinib ($C_{26}H_{23}FIN_5O_4$=615.3948 CAS: 871700-17-3)

[Chemical Formula 2]

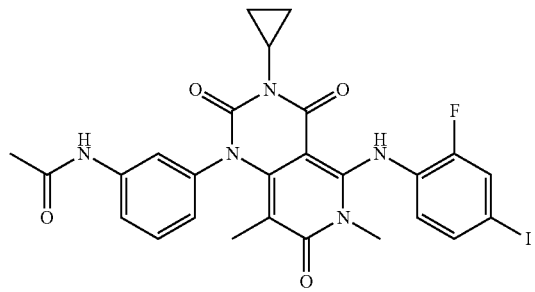

and SL327, U0126, PD184352, and PD-98059.

Wortmannin is a PI3K inhibitor for all subclasses, while trametinib specifically inhibits MEK1 and MEK2.

MEK is a gene involved in ERK-MAPK pathway (growth signaling pathway). When a ligand (growth factor) is bound to a growth factor receptor in cell membrane to obtain a dimer, signals are transmitted by MAPK pathway (MAPK cascade) in which Raf→MEK→ERK are phosphorylated through adaptor molecules and low-molecular-weight G-protein Ras. The activated ERK is ultimately transferred to nucleus to activate transcription factors, and cell growth and cell differentiation genes are expressed (ERK-MAPK pathway).

On the other hand, PI3K is a gene to be a trigger of the PI3K-Akt pathway (survival signaling pathway). Stimulation by a growth factor is transmitted simultaneously to a pathway to suppress apoptosis induction to prevent cell death. The pathway of this apoptosis-suppressing activity begins with the phosphorylation activity of PI3K, then causing the phosphorylation of Akt, and resulting in cell survival and inhibition of apoptosis induction (PI3K-Akt pathway).

A primary method for measuring kinase activity includes the following.

1) Protein is extracted from cells, an antibody specific to a target kinase existing in a sample solution is added to capture the kinase, and a substrate specific to the kinase is then added to cause an enzyme reaction.

2) Then, ADP, a product of the enzyme reaction, is measured and converted into activity.

An analysis method for determining human cancer cells sensitive to a PI3K inhibitor and/or an MEK inhibitor comprises analyzing a correspondence relationship of each inhibitor with IC50 (50% inhibitory concentration) on each cell line by using any of:

1) the ratio of the activity values of the obtained kinases (PI3K/MEK), 2) values obtained by normalizing (correcting) the activity values of the obtained kinases with the total amount of protein measured by a known method, and 3) values obtained by normalizing (correcting) the activity values of the obtained kinases with lactate dehydrogenase (LDH) measured by a known method.

By measuring and analyzing MEK and PI3K activity on a plurality of cancer cell lines, a cell line sensitive to PI3K and/or MEK inhibitors could be selected at a high probability.

Accordingly, the constitution of the present invention is as described in [1] to [26] below.

[1] A method for classifying cancer cells, which method classifies cancer cells into any of:
1) insensitive to both a PI3K inhibitor and an MEK inhibitor,
2) sensitive to a PI3K inhibitor and insensitive to an MEK inhibitor,
3) sensitive to an MEK inhibitor and insensitive to a PI3K inhibitor, or
4) sensitive to both a PI3K inhibitor and an MEK inhibitor; preferably a method for distinguishing cancer cells, which method distinguishes
1) cancer cells sensitive to a PI3K inhibitor and insensitive to an MEK inhibitor, and/or
cancer cells sensitive to an MEK inhibitor and insensitive to a PI3K inhibitor, from
2) cancer cells insensitive to both a PI3K inhibitor and an MEK inhibitor, and/or
sensitive to both a PI3K inhibitor and an MEK inhibitor;

[2] The method of [1], in which the method determines cells using the enzyme activity of PI3K and MEK in cancer cells;

[3] The method of [1] or [2], in which the method determines cells by the ratio of the enzyme activity of PI3K and MEK in cancer cells;

[4] The method of [1] or [2], in which the method further determines cells by normalization (correction) using the total amount of protein.

[5] The method of [1] or [2], in which the method further determines cells by normalization (correction) using the activity value of lactate dehydrogenase (LDH).

[6] The method of any one of [1] to [5], in which the enzyme activity is measured by capturing the enzyme using an antibody which specifically binds to PI3K or MEK.

[7] The method of any one of [1] to [6], in which the enzyme activity is measured using a substrate specific to PI3K and/or MEK.

[8] The method of any one of [1] to [7], in which the enzyme activity is carried out by measuring the amount of ADP generated.

[9] The method of any one of [1] to [8], which is used to determine the effect prediction of a PI3K inhibitor or an MEK inhibitor.

[10] The method of any one of [1] to [9], in which the PI3K inhibitor is wortmannin.

[11] The method of any one of [1] to [9], in which the MEK inhibitor is trametinib.

[12] The method of any one of [1] to [11], in which cancer cells are isolated tissue samples.

[13] The method of [12], in which the tissue sample is a biopsy tissue sample.

[14] The method of [13], in which the biopsy tissue sample is derived from a patient with triple negative breast cancer.

[15] A kit used for a method of [1] to [14], the kit including an anti-PI3K antibody and an anti-MEK antibody.

[16] A kit for measuring PI3K activity and MEK activity, the kit comprising
1) a first reagent for cytolysis, including a detergent, a protease inhibitor, and a phosphatase inhibitor,
2A) a second reagent for measuring MEK, including an anti-MEK antibody,
2B) a second reagent for measuring PI3K, including an anti-PI3K antibody,
3A) a third reagent for measuring MEK, including a substrate for MEK and ATP,
3B) a third reagent for measuring PI3K, including a substrate for PI3K and ATP,
4) a fourth reagent including D-Glucose; ADP-Hexokinase; Glucose-6-phosphate dehydrogenase; Diaphorase and NADP,
5) a fifth reagent including Luminol and Peroxidase, and
6) a sixth reagent for washing, including a detergent.

[17] The kit of [16], wherein
1) target tissue cells are lysed with the first reagent;
2A) the second reagent for measuring MEK is added to a part of the cell lysate and MEK in the target tissue cells is collected; the collected MEK is optionally washed with the sixth reagent for washing; after the third reagent for measuring MEK is then added to and reacted with the collected MEK, the fourth reagent and fifth reagent are added to and reacted with the collected MEK to measure MEK activity; and
2B) the second reagent for measuring PI3K is added to a part of the cell lysate and PI3K in the target tissue cells is collected; the collected PI3K is optionally washed with the sixth reagent for washing; after the third reagent for measuring PI3K is then added to and reacted with the collected PI3K, the fourth reagent and fifth reagent are added to and reacted with the collected PI3K to measure PI3K activity.

[18] A pharmaceutical composition for suppressing cancer cell growth, the pharmaceutical composition including a PI3K inhibitor as an active ingredient;
in which the PI3K activity/MEK activity ratio of the cancer cells is greater than the PI3K activity/MEK activity ratio of a reference standard.

[19] A PI3K inhibitor for use in the treatment of cancer including cancer cells in which the PI3K activity/MEK activity ratio is greater than the PI3K activity/MEK activity ratio of a reference standard;

[20] The use of a PI3K inhibitor in the manufacture of a medicine for suppressing the growth of cancer cells in which the PI3K activity/MEK activity ratio is greater than the PI3K activity/MEK activity ratio of a reference standard;

[21] A method for treating cancers including cancer cells in which the PI3K activity/MEK activity ratio is greater than the PI3K activity/MEK activity ratio of a reference standard, the method including administering a PI3K inhibitor to a cancer patient;

wherein, the reference standard can be a cell tissue insensitive to both a PI3K inhibitor and an MEK inhibitor or sensitive to both a PI3K inhibitor and an MEK inhibitor; and cancer cells can be breast cancer cells, preferably triple negative breast cancer cells.

[22] A pharmaceutical composition for suppressing the growth of cancer cells, the pharmaceutical composition including an MEK inhibitor as an active ingredient;

in which the PI3K activity/MEK activity ratio of the cancer cells is smaller than the PI3K activity/MEK activity ratio of a reference standard.

[23] An MEK inhibitor for use in the treatment of cancer including cancer cells in which the PI3K activity/MEK activity ratio is smaller than the PI3K activity/MEK activity ratio of a reference standard;

[24] The use of an MEK inhibitor in the manufacture of a medicine for suppressing the growth of cancer cells in which the PI3K activity/MEK activity ratio is smaller than the PI3K activity/MEK activity ratio of a reference standard;

[25] A method for treating a cancer including cancer cells in which the PI3K activity/MEK activity ratio is smaller than the PI3K activity/MEK activity ratio of a reference standard, the method including administering an MEK inhibitor to a cancer patient;

Herein, the reference standard can be a cell tissue insensitive to both a PI3K inhibitor and an MEK inhibitor or sensitive to both a PI3K inhibitor and an MEK inhibitor; and cancer cells can be breast cancer cells, preferably triple negative breast cancer cells.

[26] A method for diagnosing and treating cancers, the method including, 1) collecting a cancer cell tissue from a patient,
2) measuring the MEK activity and PI3K activity in the collected cancer cells, and
3) administering a PI3K inhibitor to the patient when the PI3K activity/MEK activity ratio is greater than the PI3K activity/MEK activity ratio of a reference standard; and administering an MEK inhibitor to the patient when the PI3K activity/MEK activity ratio is smaller than the PI3K activity/MEK activity ratio of a reference standard;

Herein, the reference standard can be a cell tissue insensitive to both a PI3K inhibitor and an MEK inhibitor or sensitive to both a PI3K inhibitor and an MEK inhibitor; and cancer can be breast cancer, preferably triple negative breast cancer.

[27] A use of the PI3K activity/MEK activity ratio as a predictive factor for an effect of an anticancer drug on a cancer.

[28] The use of [27], in which the anticancer drug is a PI3K inhibitor or/and an MEK inhibitor.

[29] The use of [27] or [28], in which the cancer is triple negative breast cancer.

Advantageous Effect of Invention

The development of drugs to inhibit kinases and the development of companion diagnostics involved therein have actively advanced. As diagnostics, there is a method in which the expression levels and mutational patterns of genes related to signal transduction are confirmed, which method is actually in clinical use.

Various drugs which directly inhibit kinase activity have been developed as molecular targeted drugs in the development of anticancer drugs; however, there does not exist diagnostics to directly evaluate their effectiveness, i.e. the inhibition degree of kinase activity, and known companion diagnostics includes only methods for measuring indirect factors such as the expression levels, expression patterns and mutational patterns of cancer related genes, and the phosphorylation patterns and phosphorylation levels of molecules contained in signal transduction pathways. In an analysis using those factors measured, information enough to predict the effect of each molecular targeted drug cannot be necessarily provided.

In such circumstances, the invention of the application provides a novel study approach and a novel method for classifying cancer cells based on the approach, and can contribute to the development of drugs to inhibit kinases and the development of companion diagnostics related thereto.

A growth inhibition rate of 25% in a drug concentration of 1 µM was used as an index.

Figure 1A:
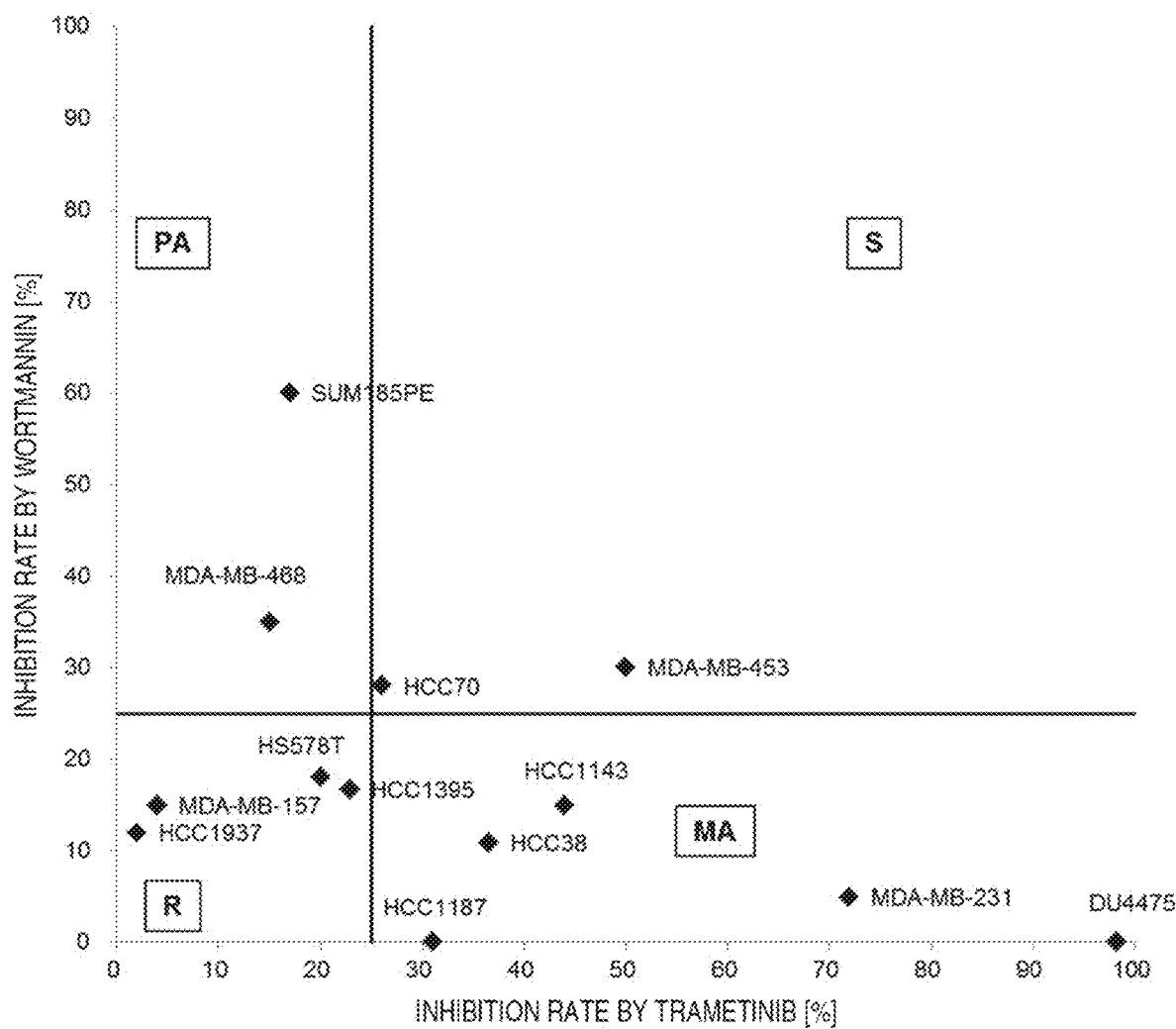
FIG. 1A: Classification of cell lines by the inhibition rate of each drug.
Figure 1B:
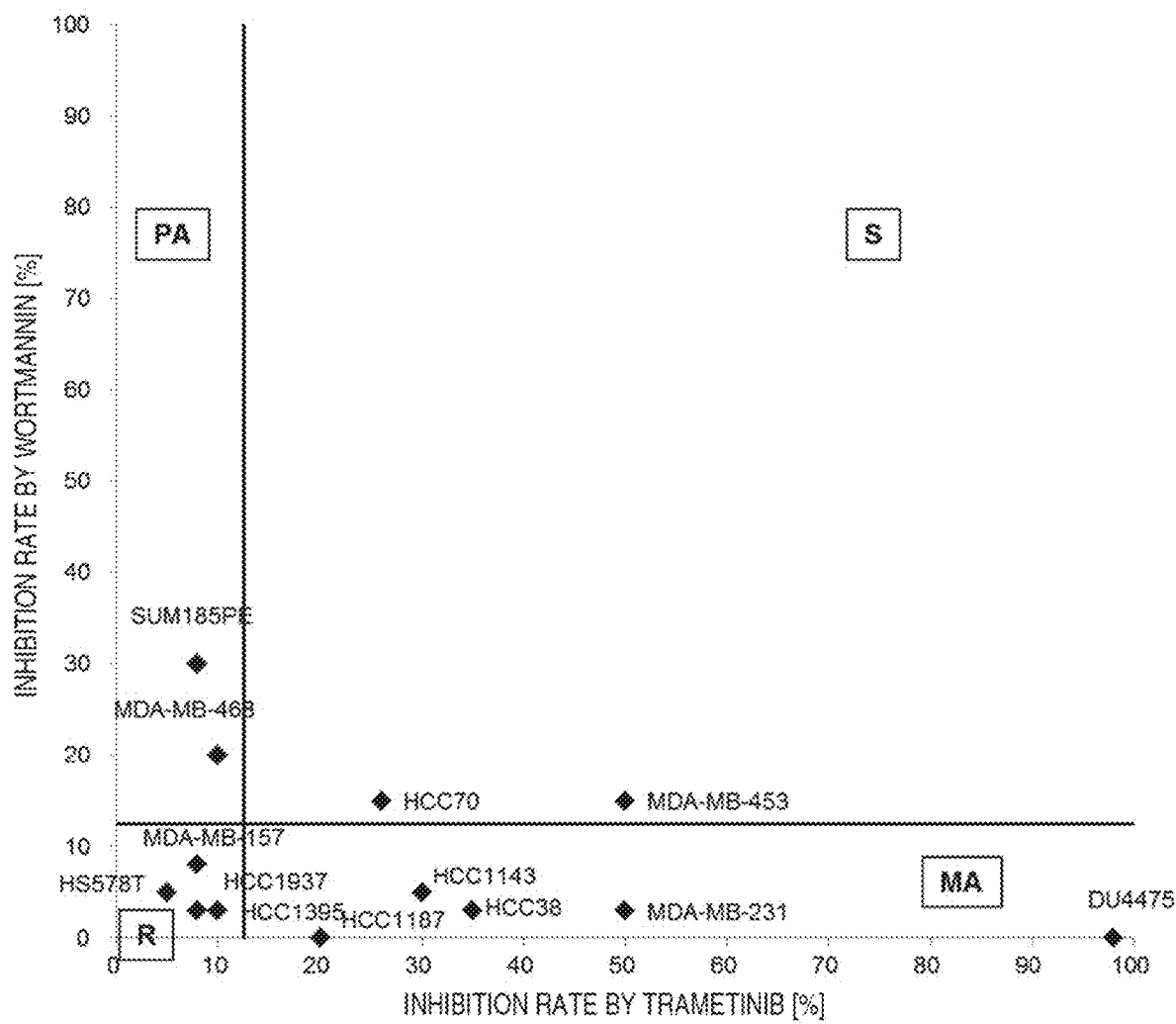

FIG. 1B: Classification of cell lines by the inhibition rate of each drug.

A growth inhibition rate of 12.5% in a drug concentration of 100 nM was used as an index.

Figure 1C:
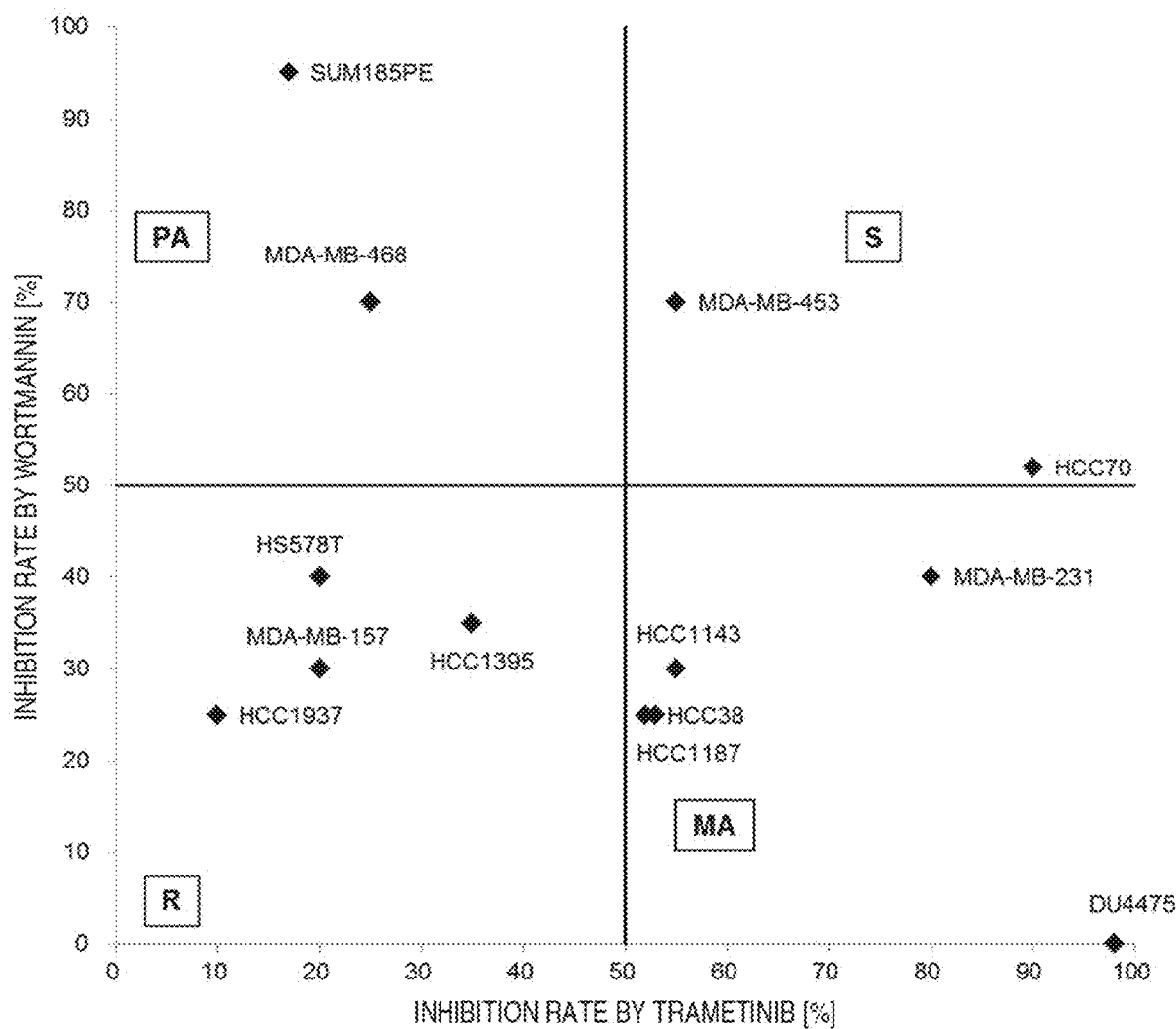

FIG. 1C: Classification of cell lines by the inhibition rate of each drug.

A growth inhibition rate of 50% in a drug concentration of 10 µM was used as an index.

Figure 2:
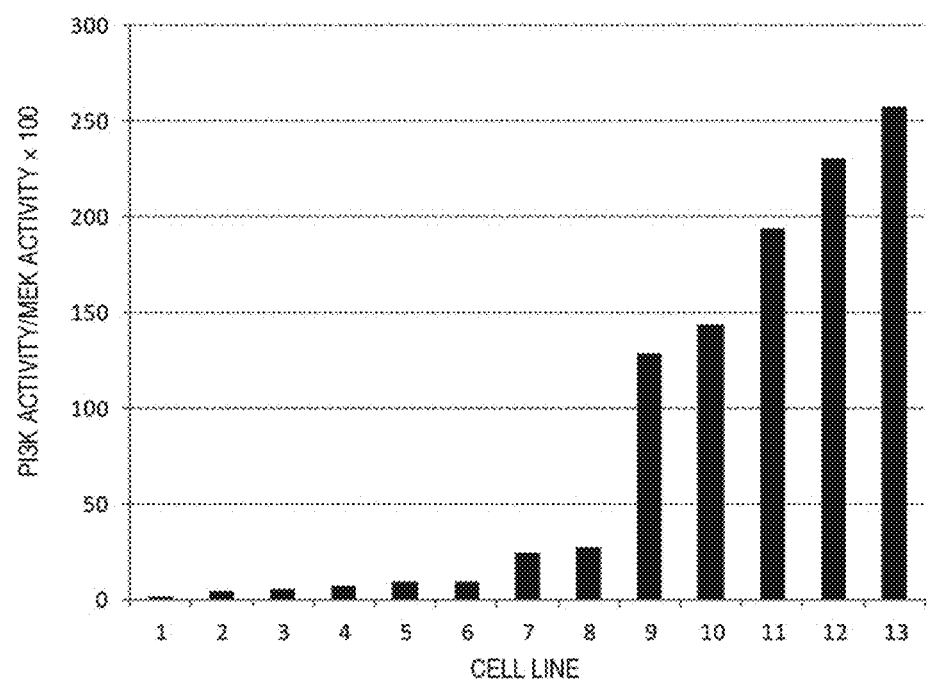

FIG. 2: Comparison with cell classification by PI3K activity/MEK activity values.

Figure 3:
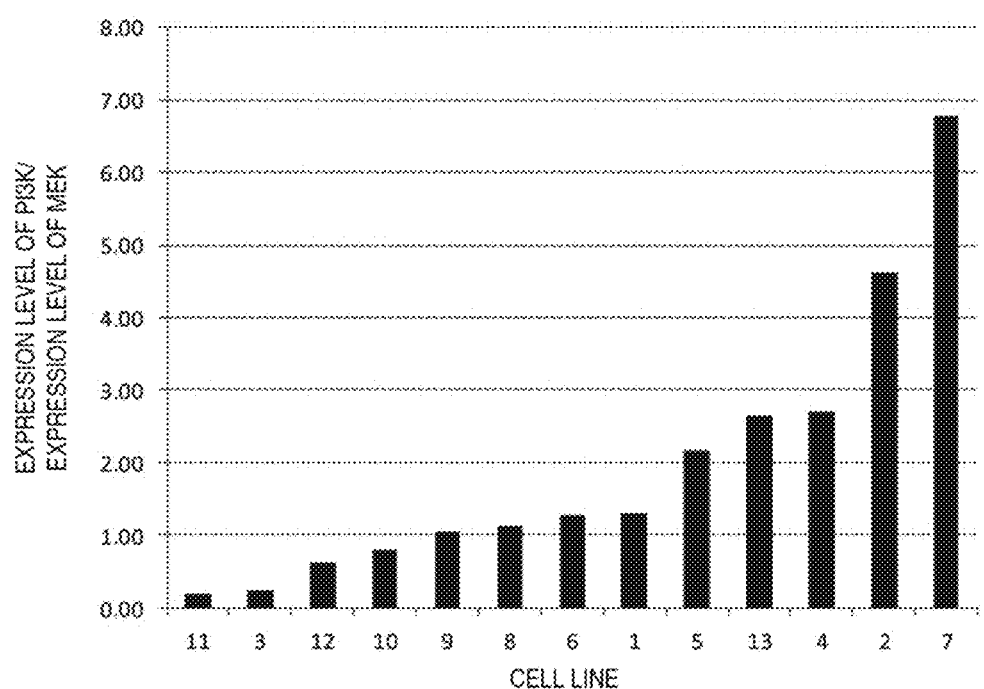

FIG. 3: Comparison with cell classification by values of the expression level of PI3K/the expression level of MEK (Comparative Example 1).

Figure 4:
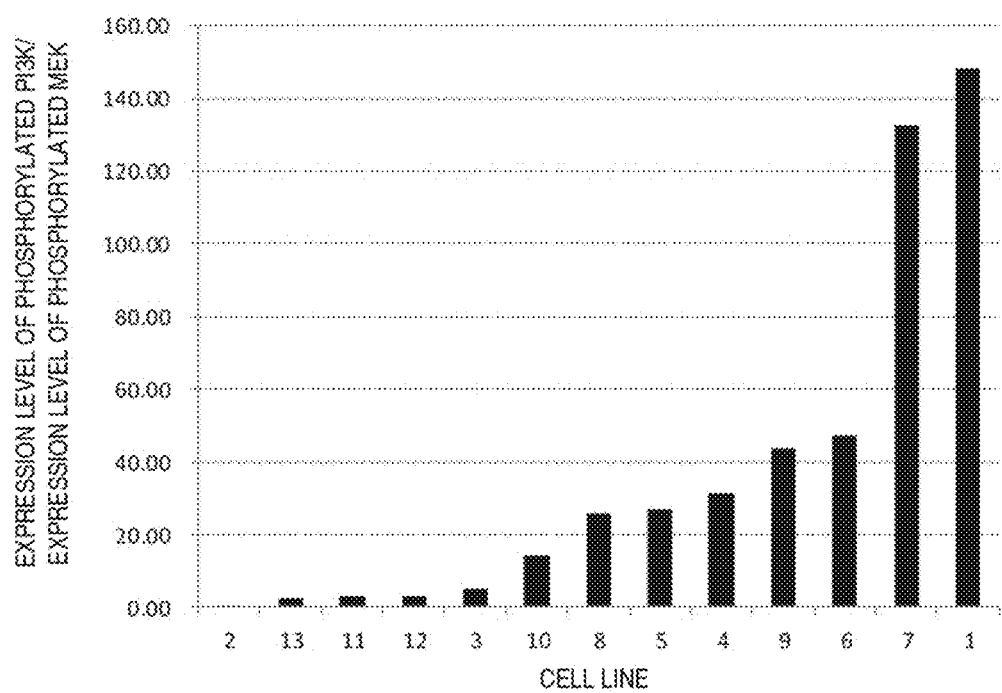

FIG. 4: Comparison with cell classification by values of the expression level of phosphorylated PI3K/the expression level of phosphorylated MEK (Comparative Example 2).

Figure 5:
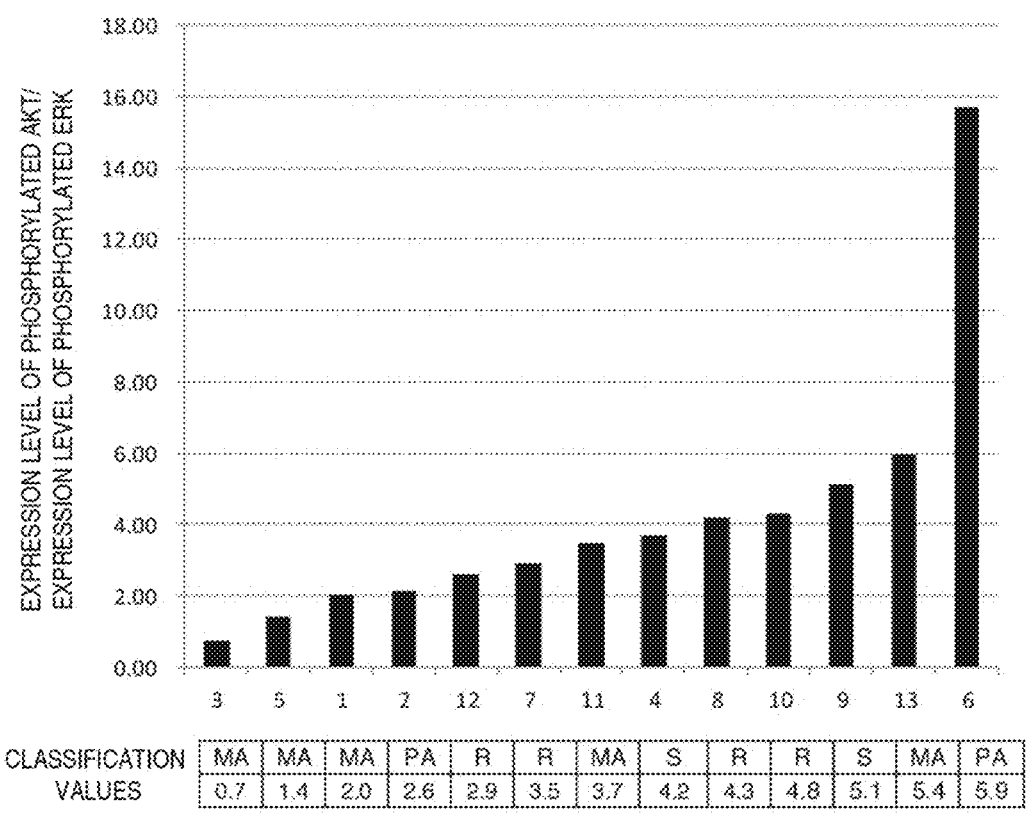

FIG. 5: Comparison with cell classification by values of the expression level of phosphorylated AKT/the expression level of phosphorylated ERK (Comparative Example 3).

Figure 6:
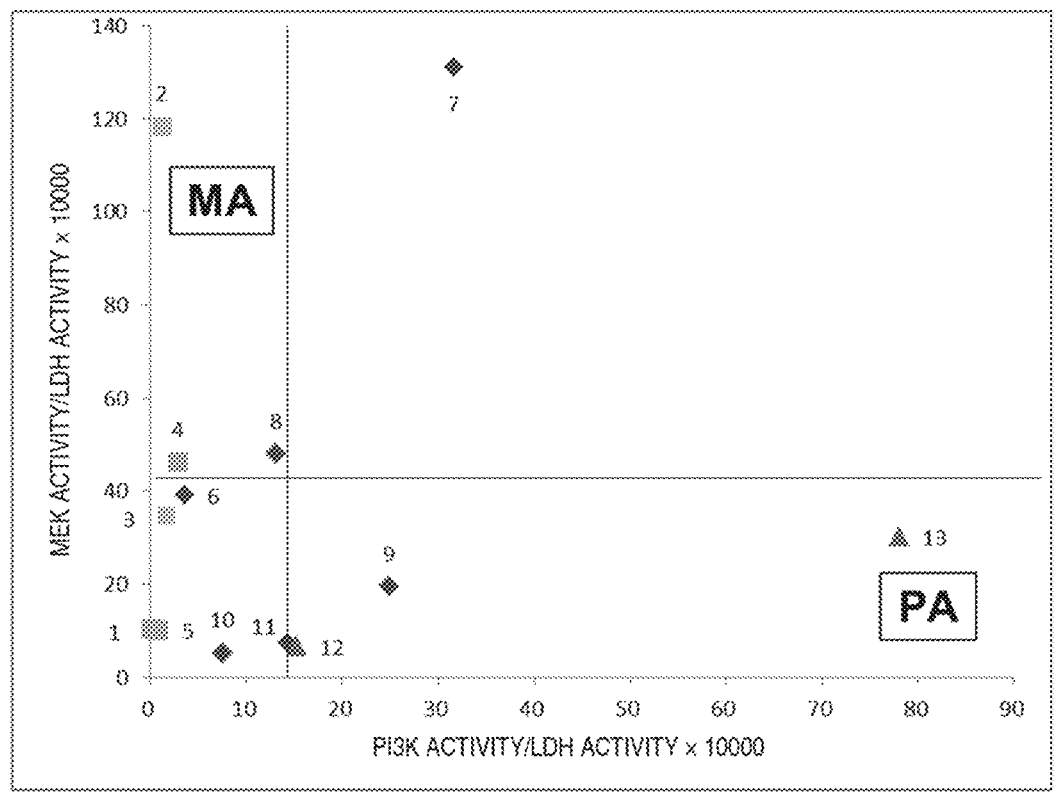

FIG. 6: Grid analysis by X: PI3K activity/LDH activity, and Y: MEK activity/LDH activity.

Figure 7:
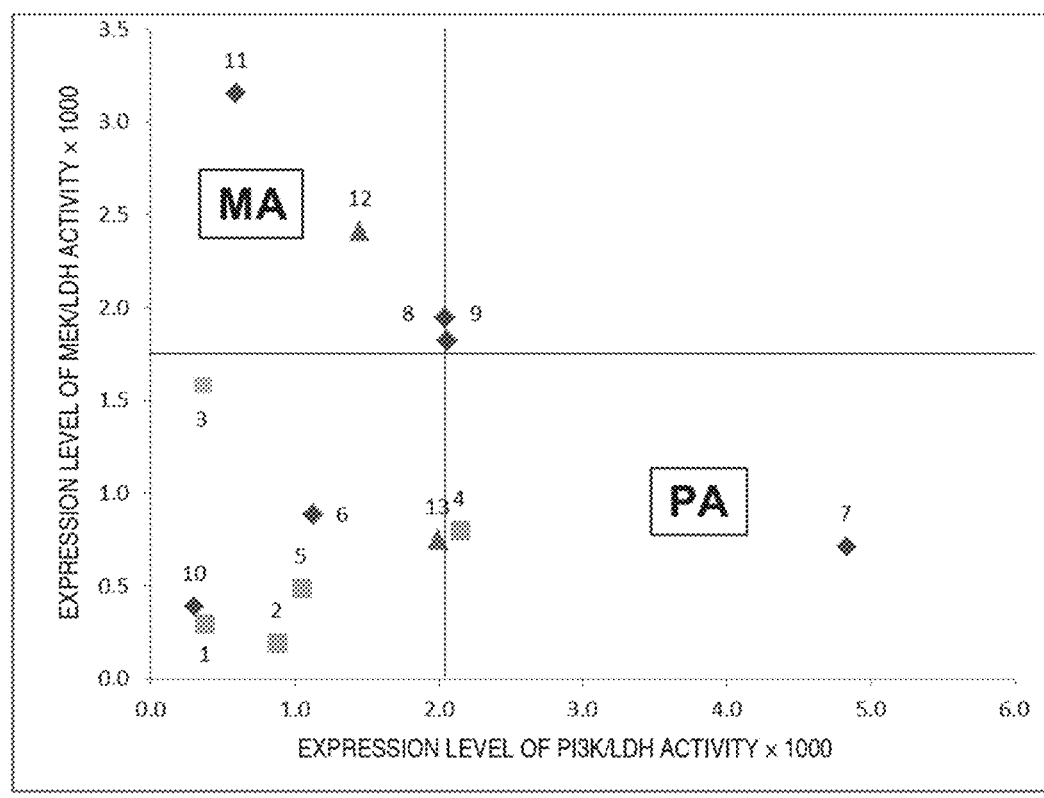

FIG. 7: Grid analysis by X: the expression level of PI3K/LDH activity, and Y: the expression level of MEK/LDH activity (Comparative Example 4)

Figure 8:
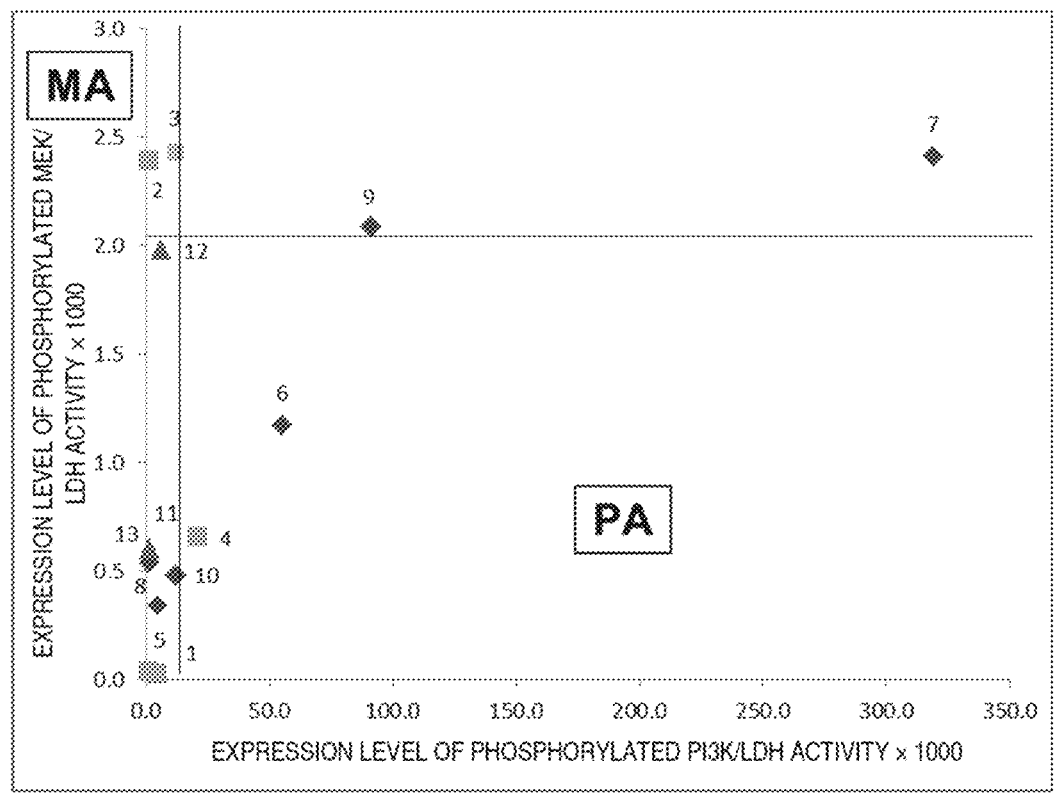

FIG. 8: Grid analysis by X: the expression level of phosphorylated PI3K/LDH activity, and Y: the expression level of phosphorylated MEK/LDH activity (Comparative Example 5).

Figure 9:
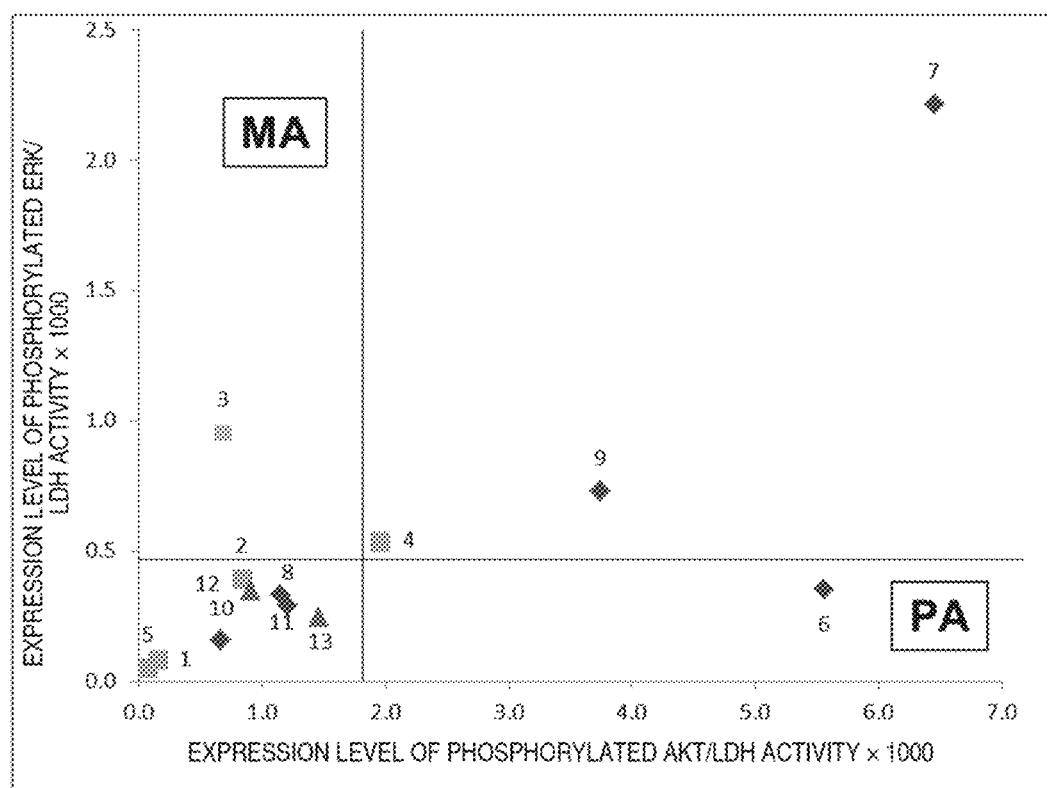

FIG. 9: Grid analysis by X: the expression level of phosphorylated AKT/LDH activity, and Y: the expression level of phosphorylated ERK/LDH activity (Comparative Example 6).

Figure 10:
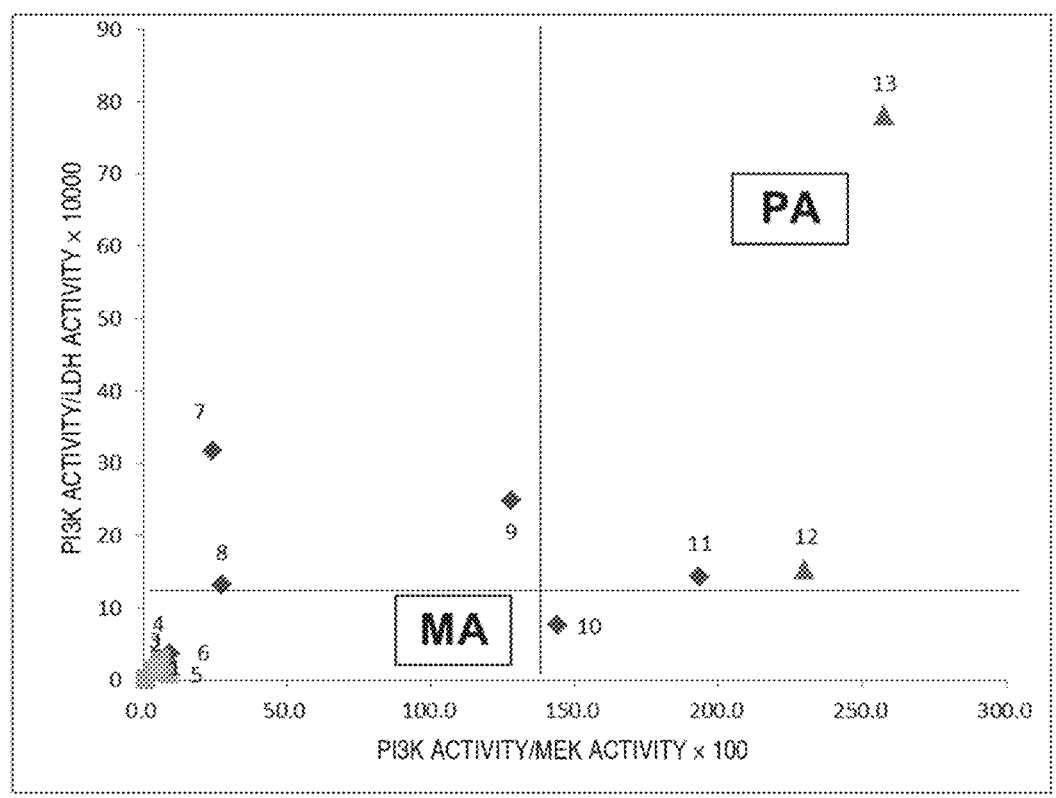

FIG. 10: Grid analysis by X: PI3K activity/MEK activity, and Y: PI3K activity/LDH activity.

Figure 11:
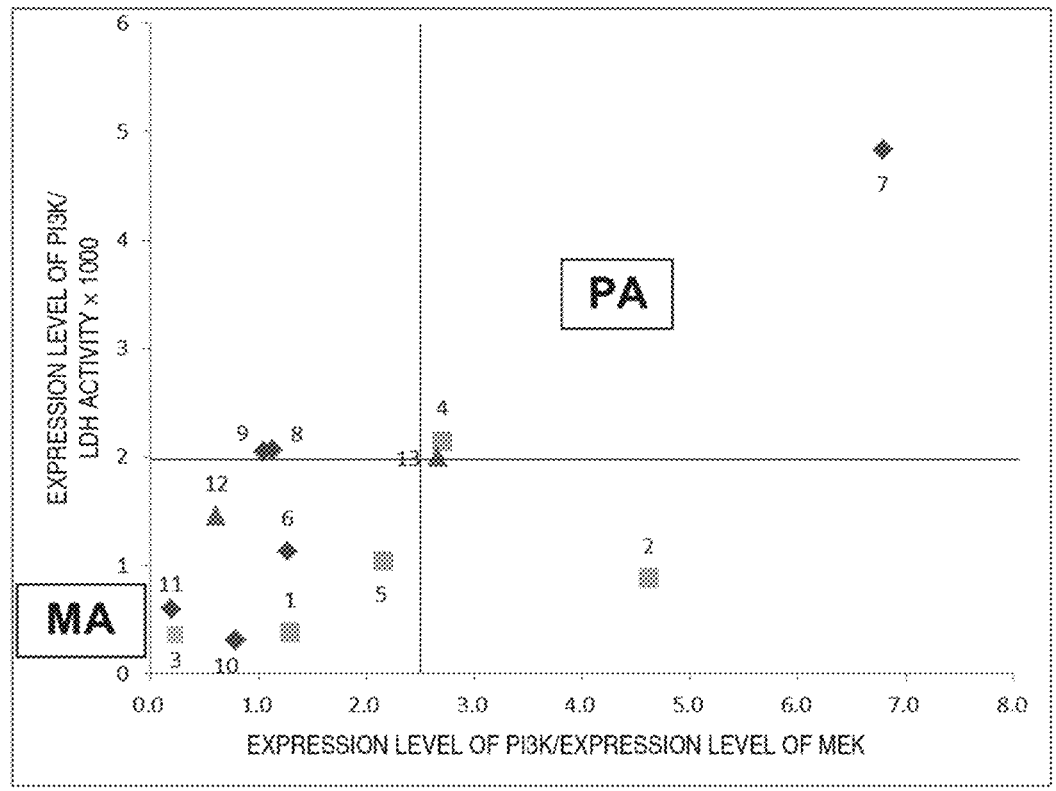

FIG. 11: Grid analysis by X: the expression level of PI3K/the expression level of MEK, and Y: the expression level of PI3K/LDH activity (Comparative Example 7).

Figure 12:
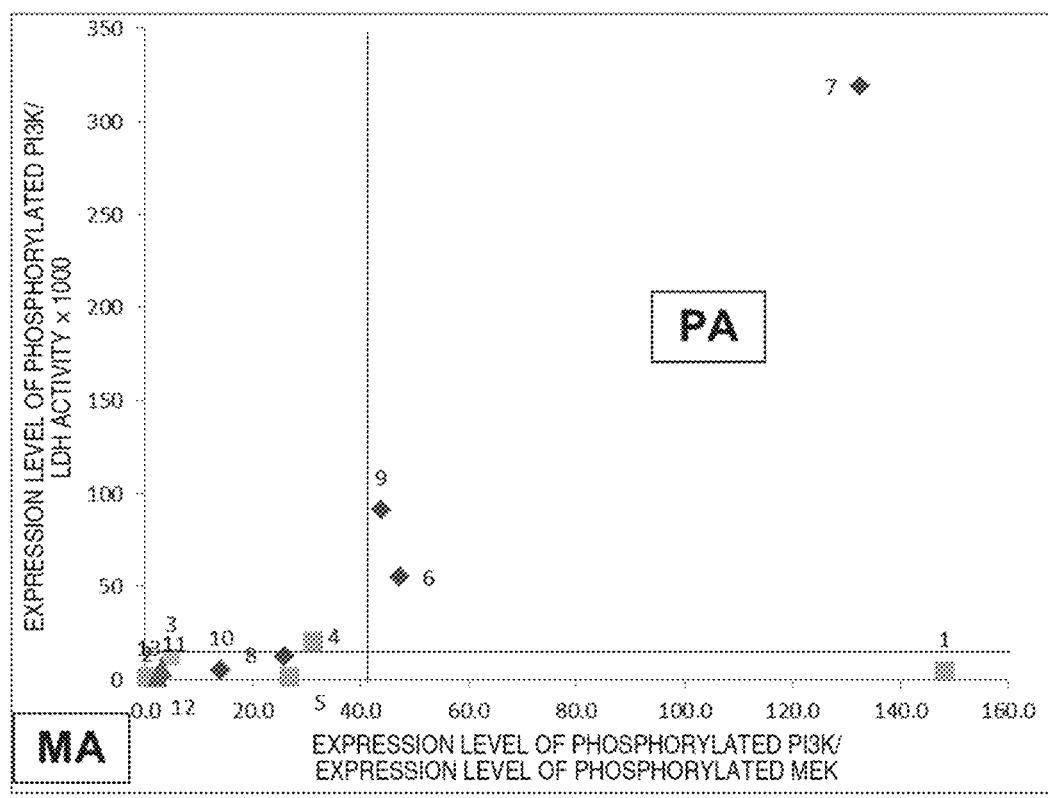

FIG. 12: Grid analysis by X: the expression level of phosphorylated PI3K/the expression level of phosphorylated MEK, and Y: the expression level of phosphorylated PI3K/LDH activity (Comparative Example 8).

Figure 13:
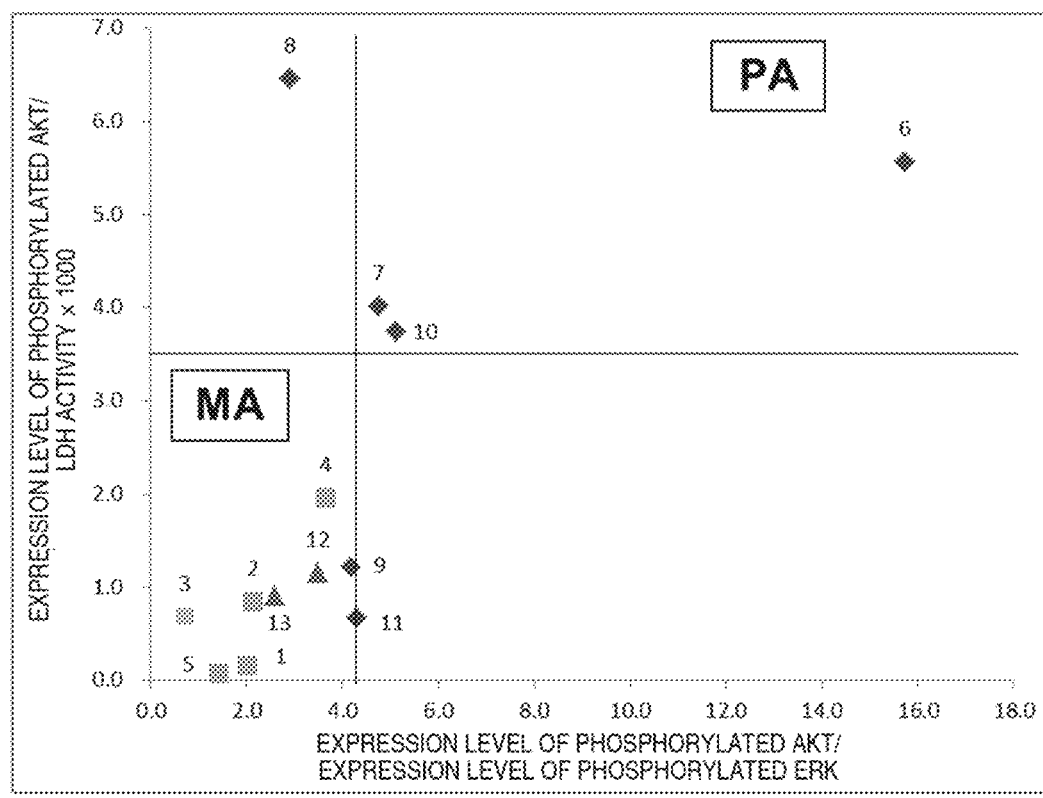

FIG. 13: Grid analysis by X: the expression level of phosphorylated AKT/the expression level of phosphorylated ERK, and Y: the expression level of phosphorylated AKT/LDH activity (Comparative Example 9).

Figure 14:
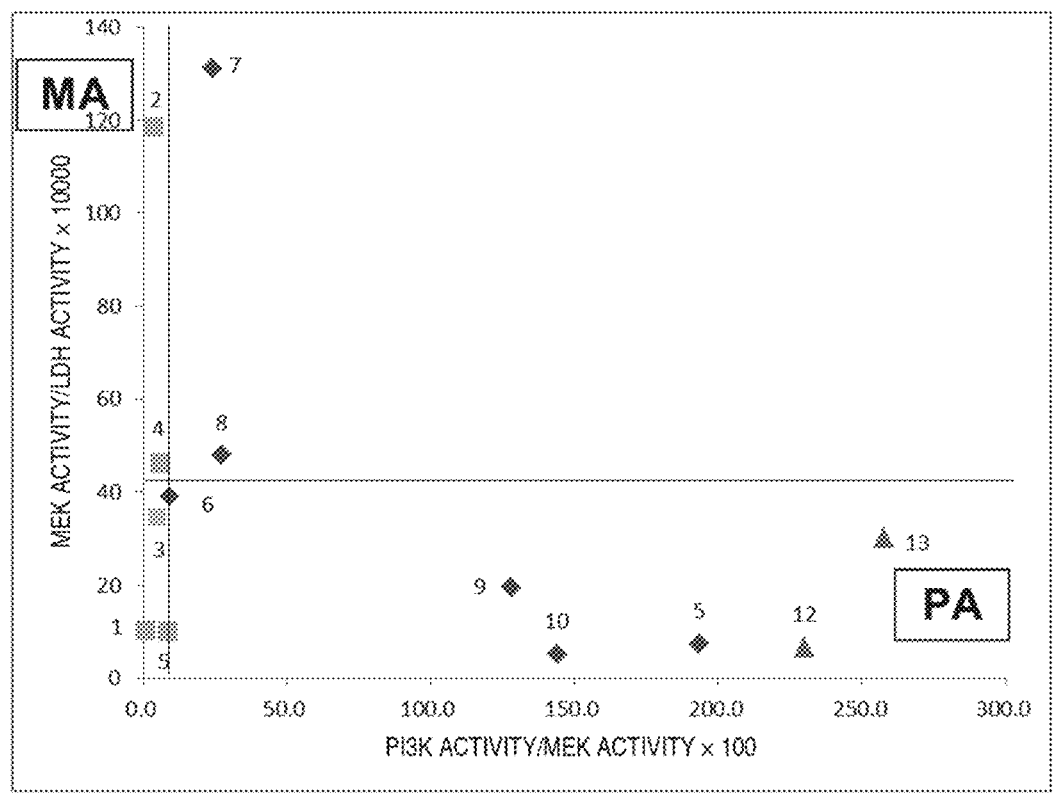

FIG. 14: Grid analysis by X: PI3K activity/MEK activity, and Y: MEK activity/LDH activity.

Figure 15:
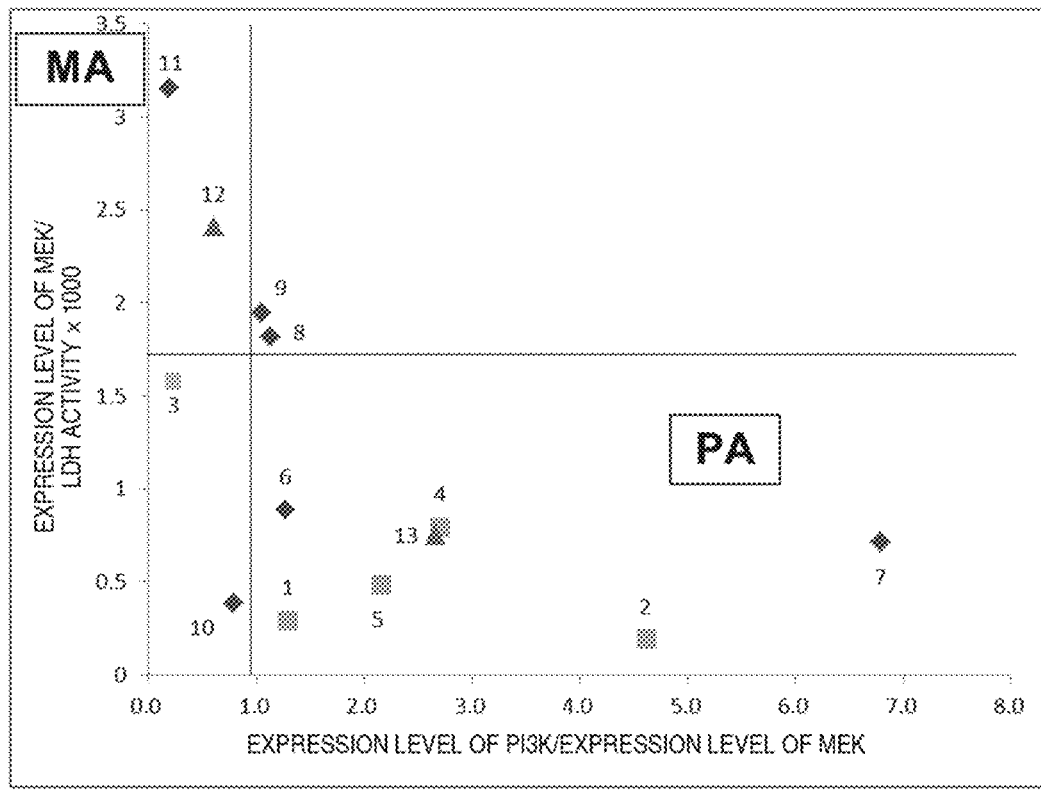

FIG. 15: Grid analysis by X: the expression level of PI3K/the expression level of MEK, and Y: the expression level of MEK/LDH activity (Comparative Example 10).

Figure 16:
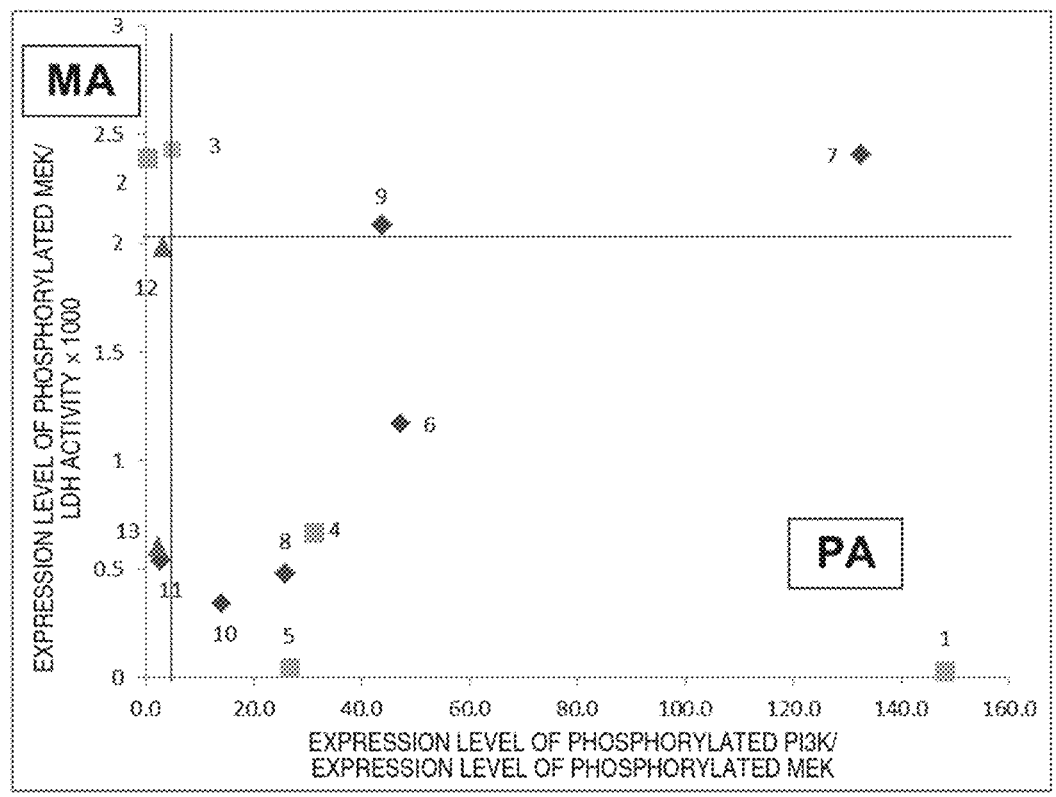

FIG. 16: Grid analysis by X: the expression level of phosphorylated PI3K/the expression level of phosphorylated MEK, and Y: the expression level of phosphorylated MEK/LDH activity (Comparative Example 11).

Figure 17:
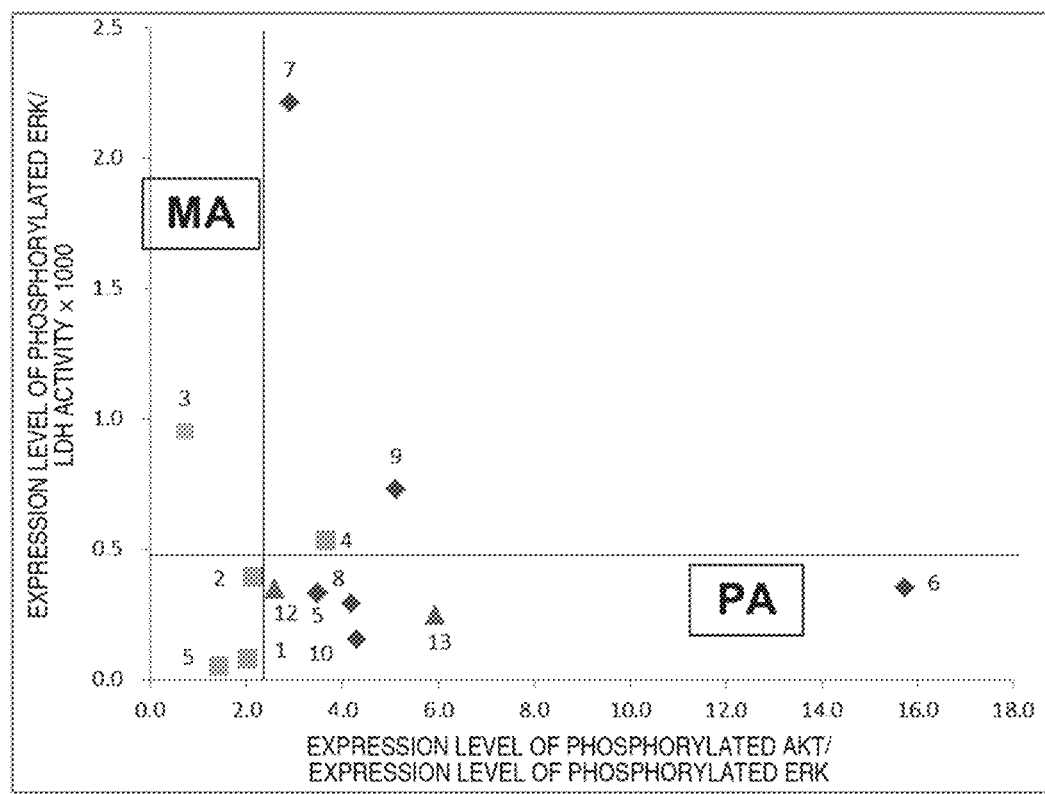

FIG. 17: Grid analysis by X: the expression level of phosphorylated AKT/the expression level of phosphorylated ERK, and Y: the expression level of phosphorylated ERK/LDH activity (Comparative Example 12).

Figure 18:
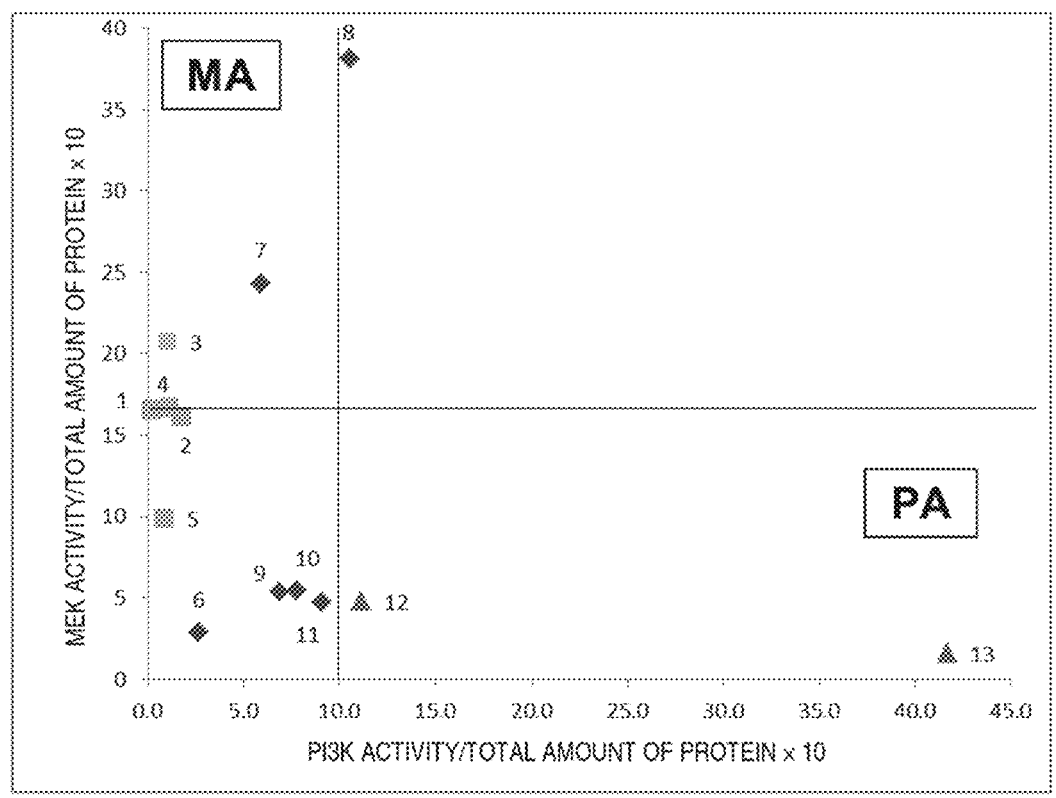

FIG. 18: Grid analysis by X: PI3K activity/the total amount of protein, and Y: MEK activity/the total amount of protein.

Figure 19:
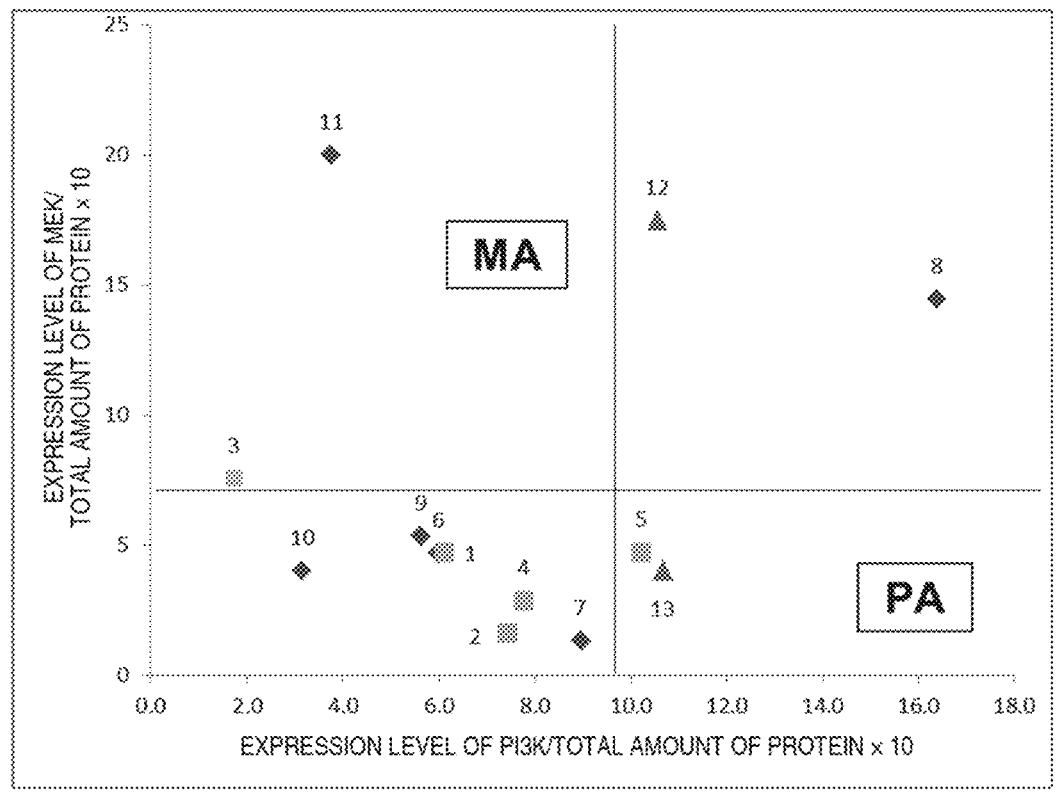

FIG. 19: Grid analysis by X: the expression level of PI3K/the total amount of protein, and Y: the expression level of MEK/the total amount of protein (Comparative Example 13).

Figure 20:
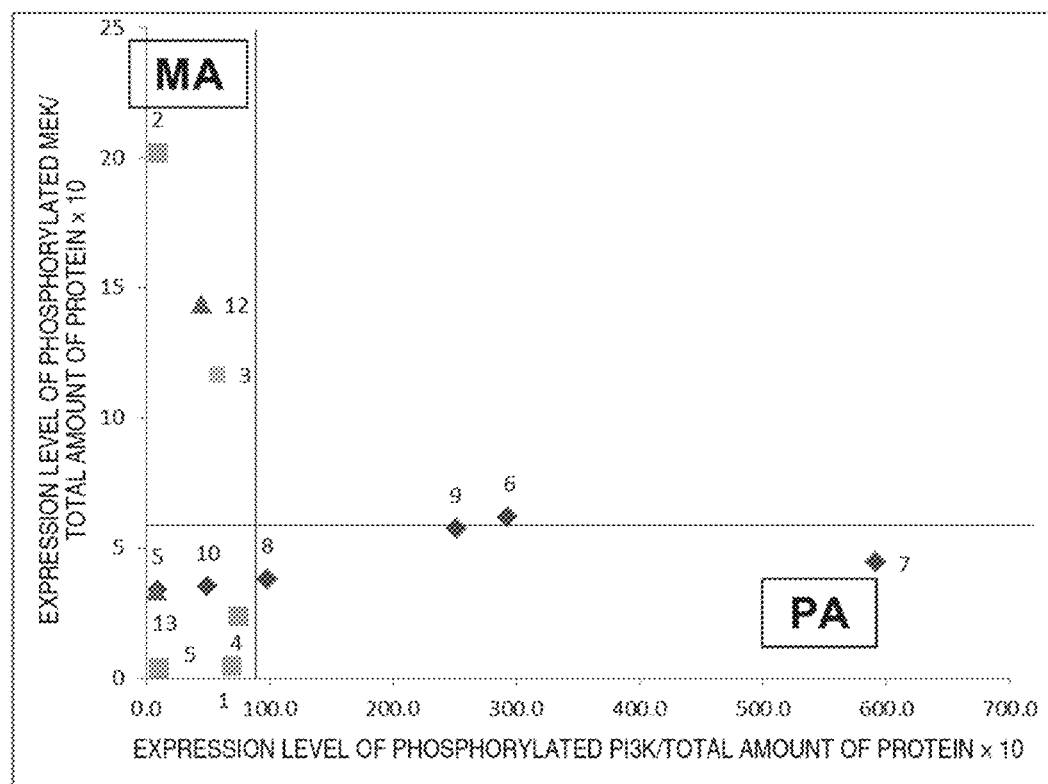

FIG. 20: Grid analysis by X: the expression level of phosphorylated PI3K/the total amount of protein, and Y: the expression level of phosphorylated MEK/the total amount of protein (Comparative Example 14).

Figure 21:
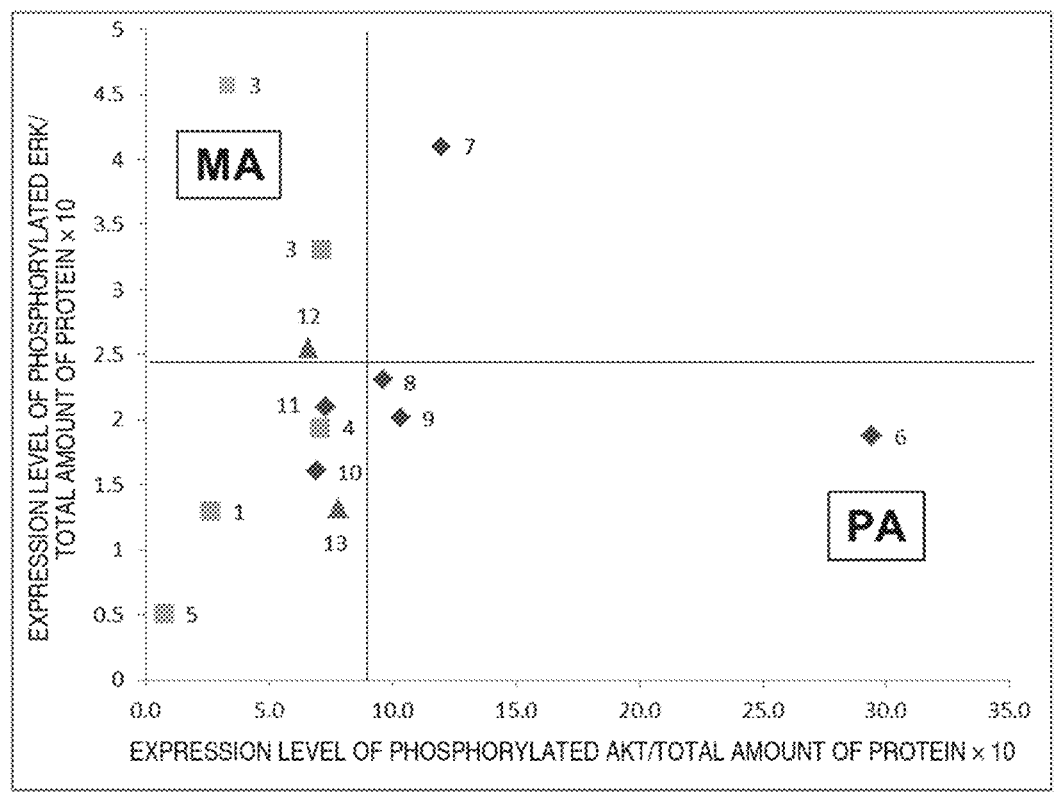

FIG. 21: Grid analysis by X: the expression level of phosphorylated AKT/the total amount of protein, and Y: the expression level of phosphorylated ERK/the total amount of protein (Comparative Example 15).

Figure 22:
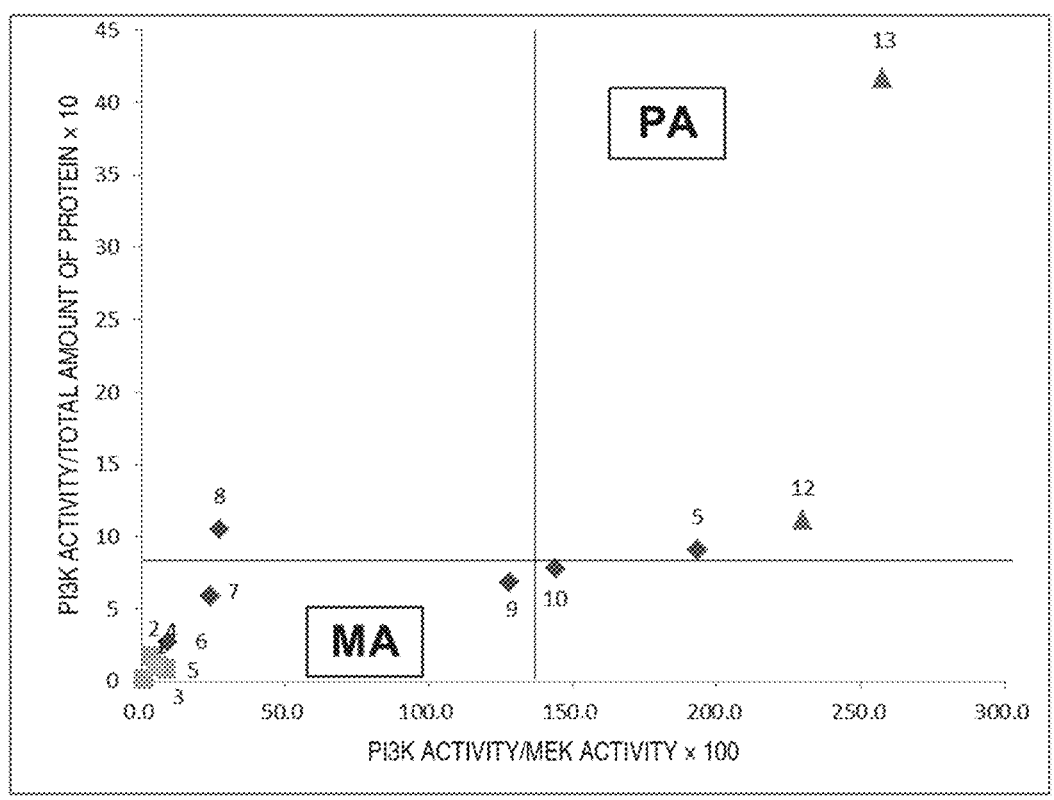

FIG. 22: Grid analysis by X: PI3K activity/MEK activity, and Y: PI3K activity/the total amount of protein.

Figure 23:
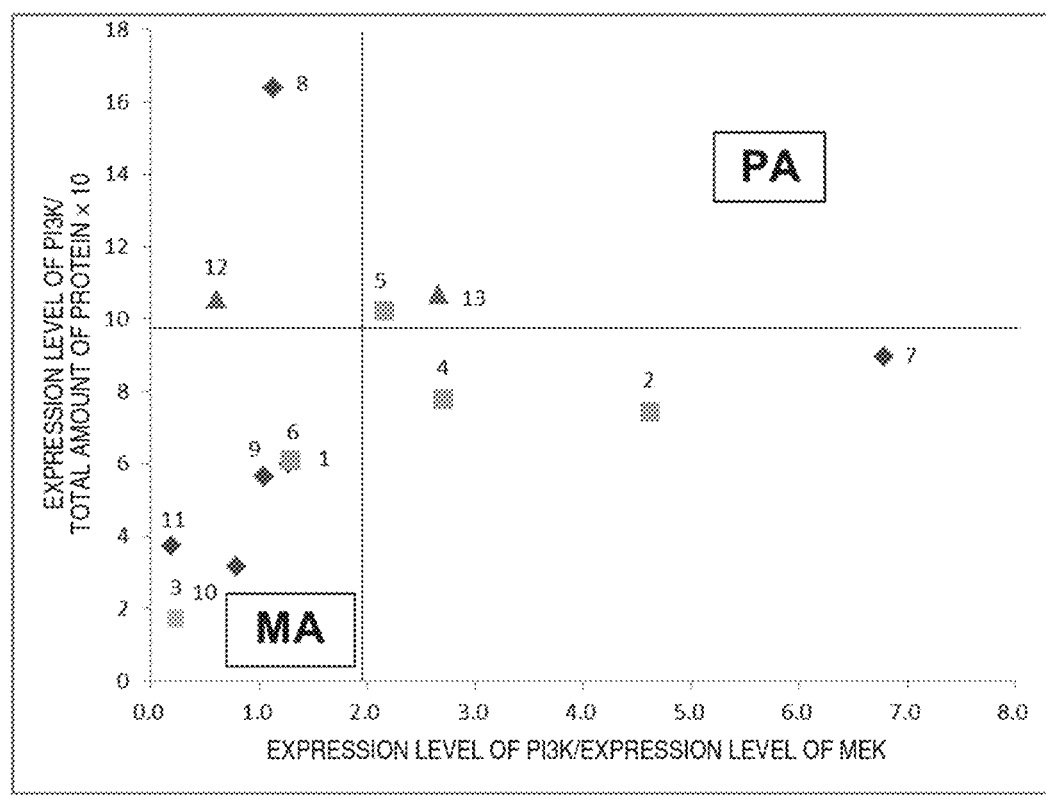

FIG. 23: Grid analysis by X: the expression level of PI3K/the expression level of MEK, and Y: the expression level of PI3K/the total amount of protein (Comparative Example 16).

Figure 24:
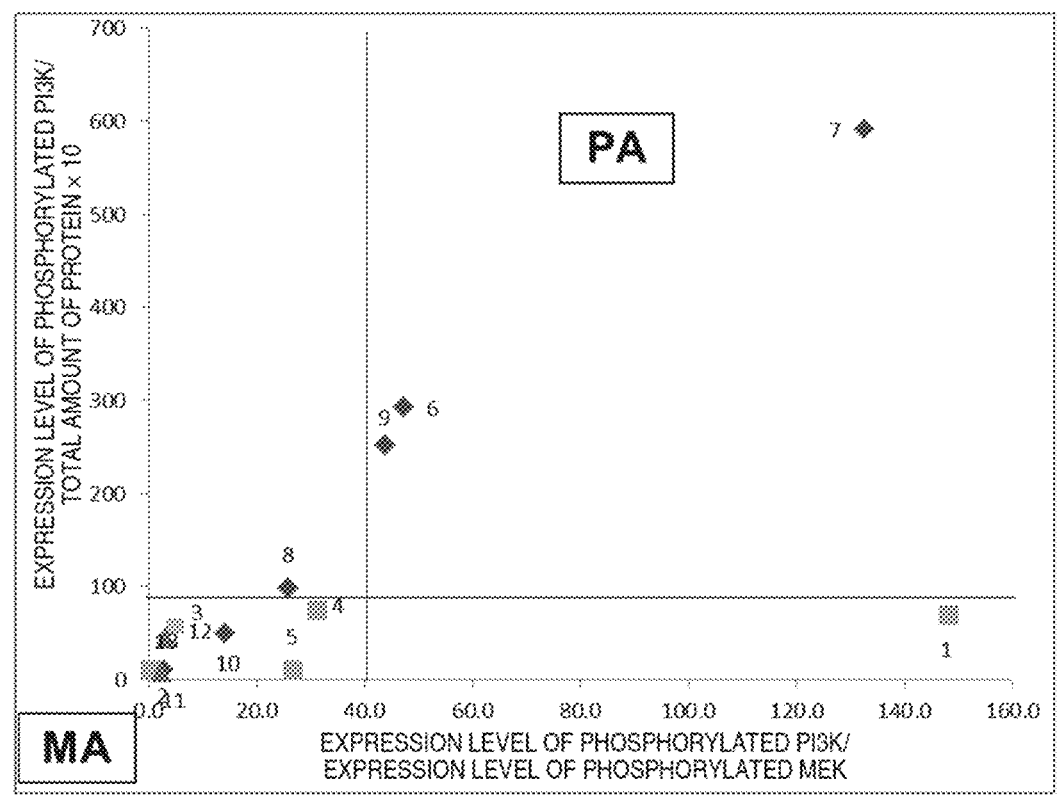

FIG. 24: Grid analysis by X: the expression level of phosphorylated PI3K/the expression level of phosphorylated MEK, and Y: the expression level of phosphorylated PI3K/the total amount of protein (Comparative Example 17).

Figure 25:
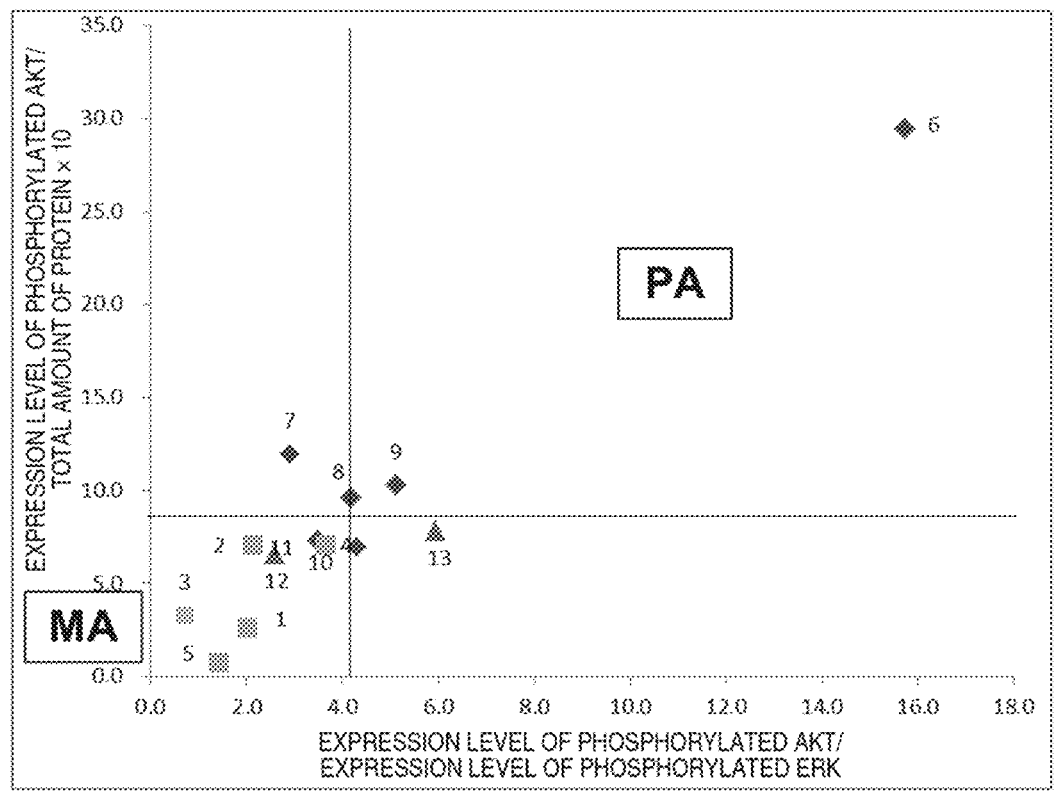

FIG. 25: Grid analysis by X: the expression level of phosphorylated AKT/the expression level of phosphorylated ERK, and Y: the expression level of phosphorylated AKT/the total amount of protein (Comparative Example 18).

Figure 26:
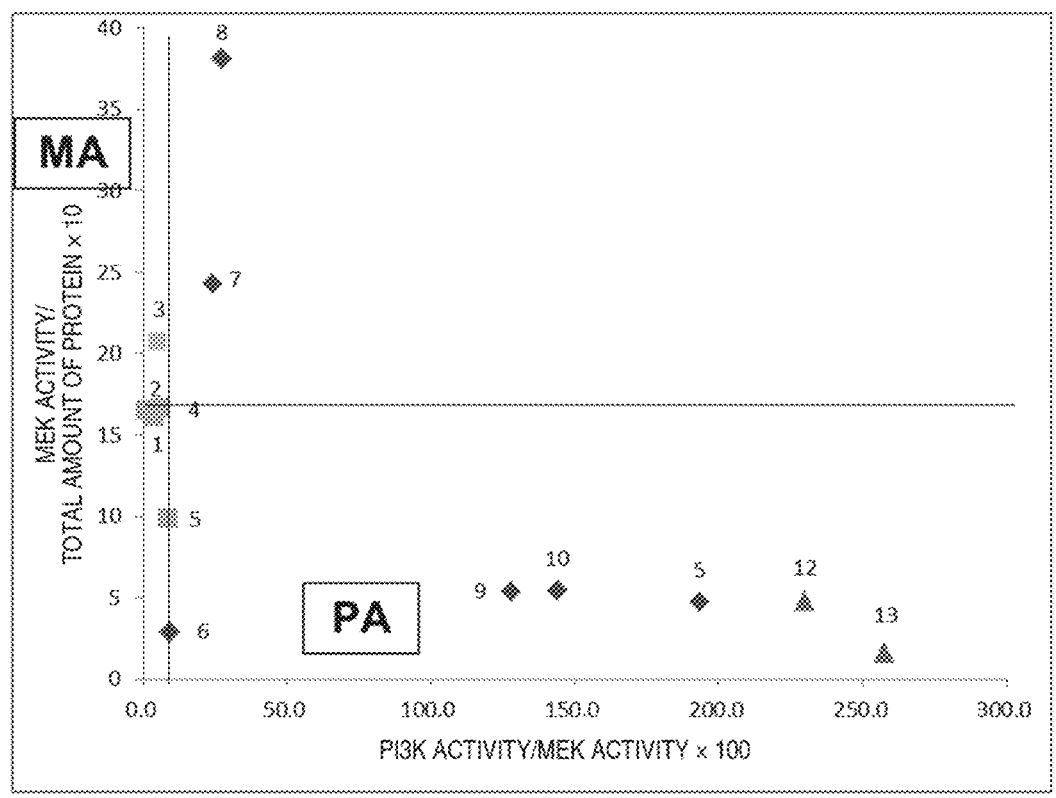

FIG. 26: Grid analysis by X: PI3K activity/MEK activity, and Y: MEK activity/the total amount of protein.

Figure 27:
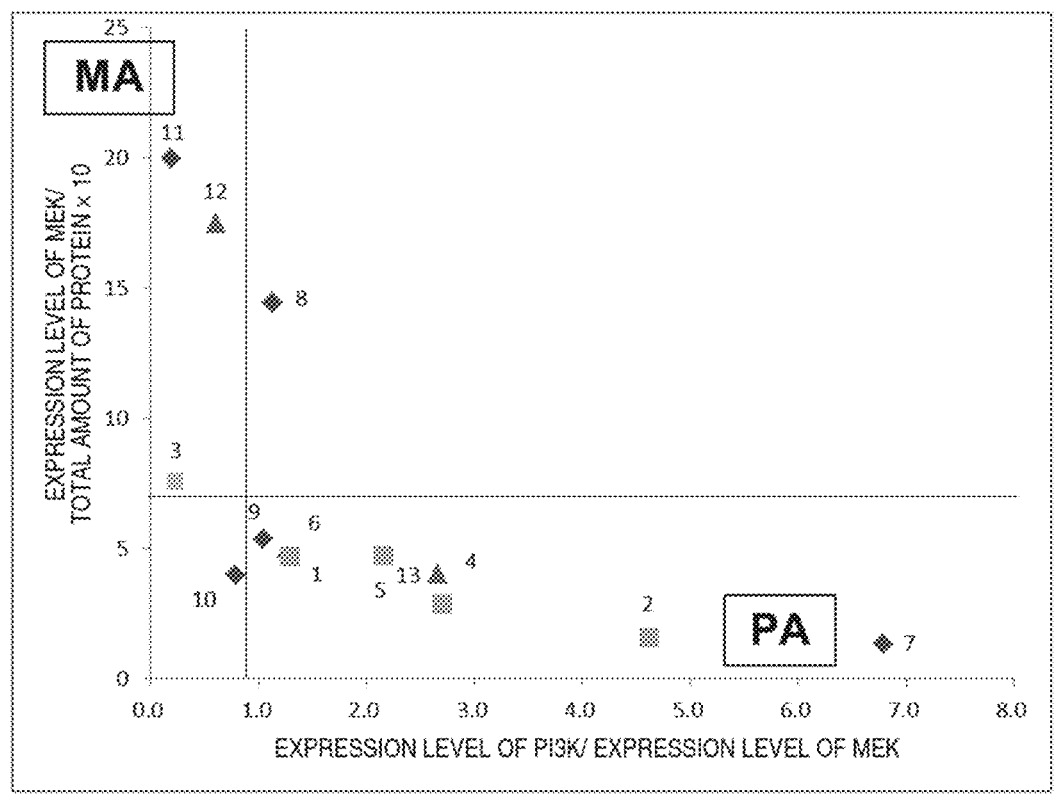

FIG. 27: Grid analysis by X: the expression level of PI3K/the expression level of MEK, and Y: the expression level of MEK/the total amount of protein (Comparative Example 19).

Figure 28:
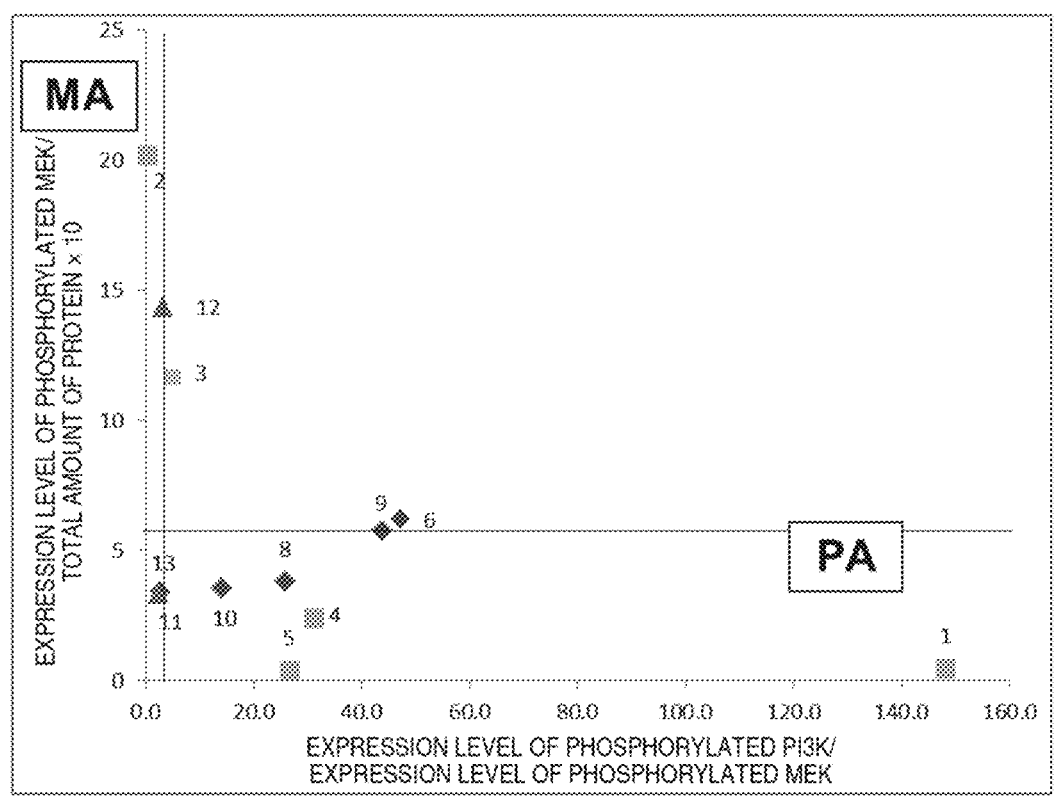

FIG. 28: Grid analysis by X: the expression level of phosphorylated PI3K/the expression level of phosphorylated MEK, and Y: the expression level of phosphorylated MEK/the total amount of protein (Comparative Example 20).

Figure 29:
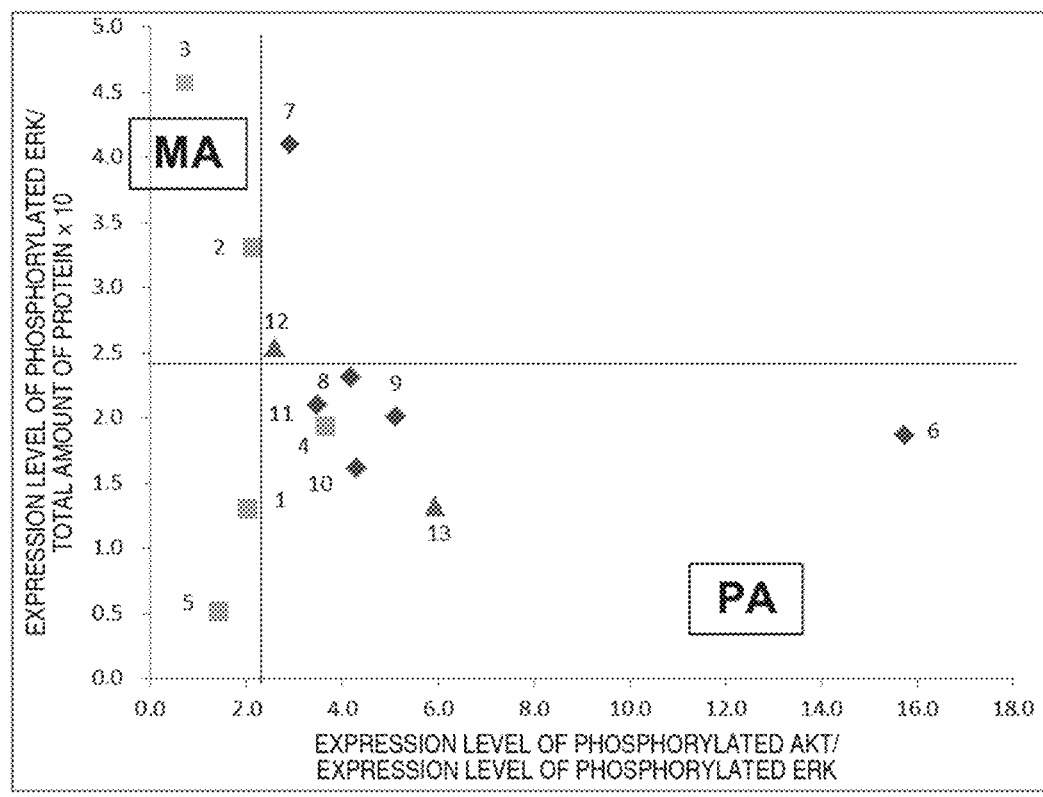

FIG. 29: Grid analysis by X: the expression level of phosphorylated AKT/the expression level of phosphorylated ERK, and Y: the expression level of phosphorylated ERIK/the total amount of protein (Comparative Example 21).

Figure 30:
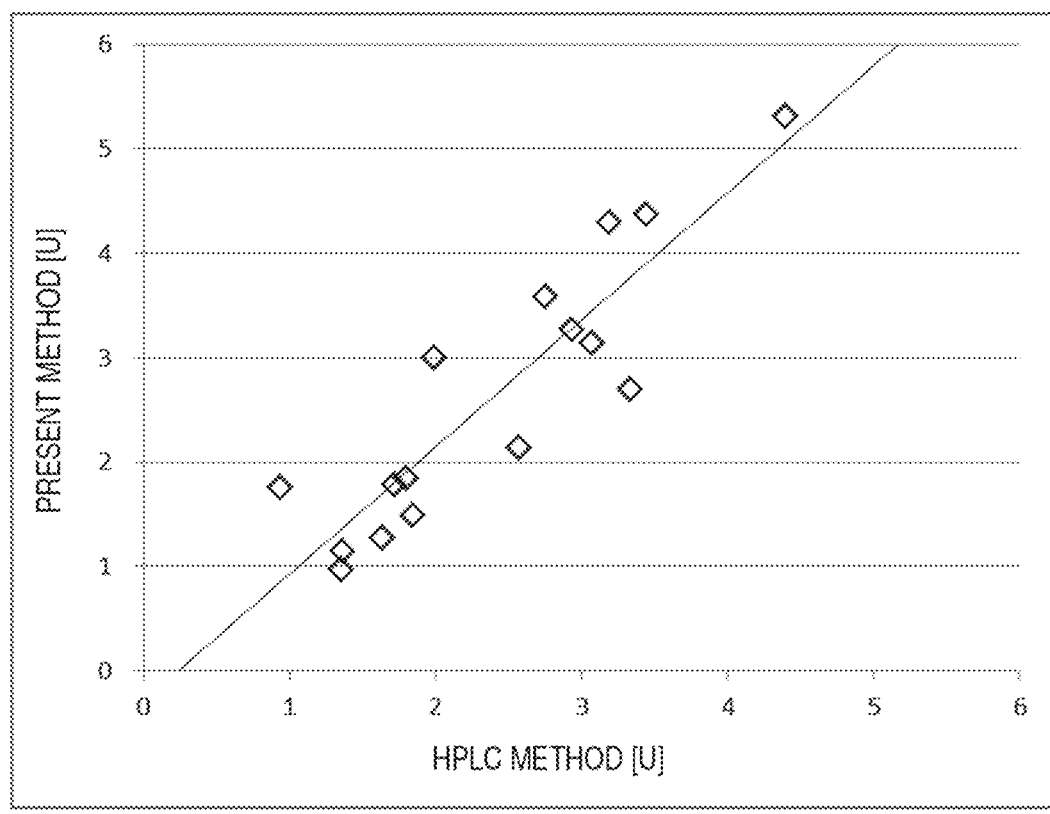

FIG. 30: Correlation with HPLC method in the measurement of MEK activity.

Figure 31:
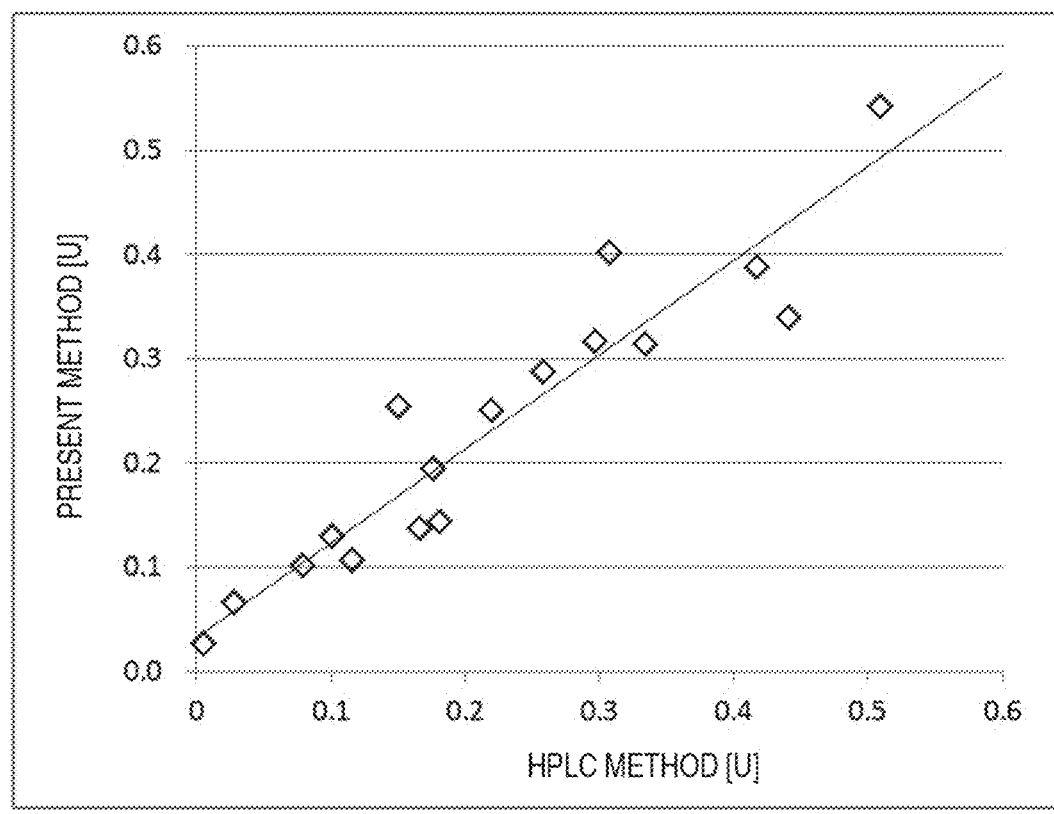

FIG. 31: Correlation with HPLC method in the measurement of PI3K activity.

Figure 32:
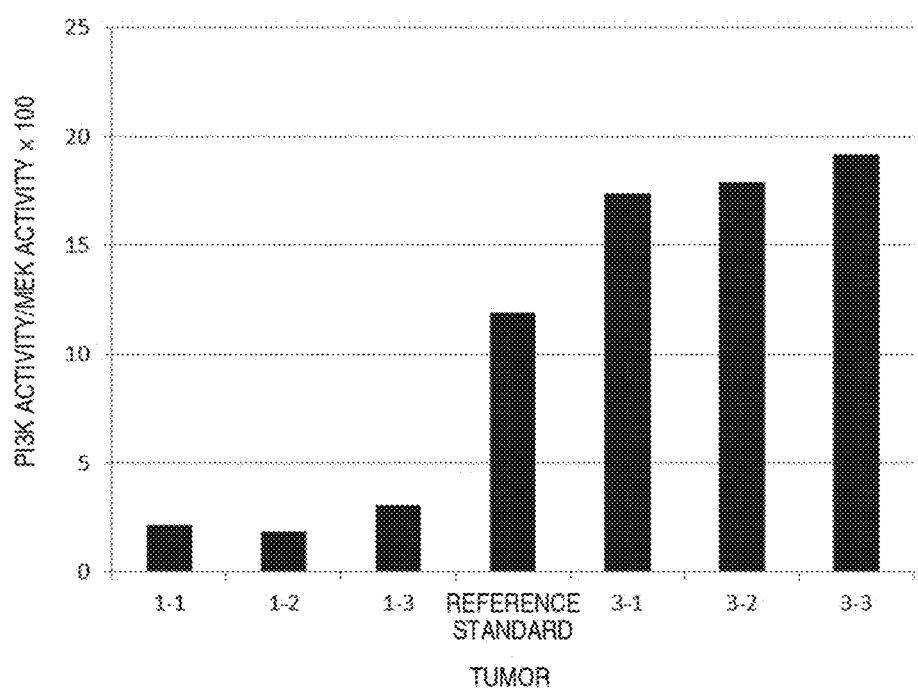

FIG. 32: the ratio of kinase activity (PI3K activity/MEK activity) in tumors resected from tumor-bearing mice prepared from cultured cells.

Figure 33:
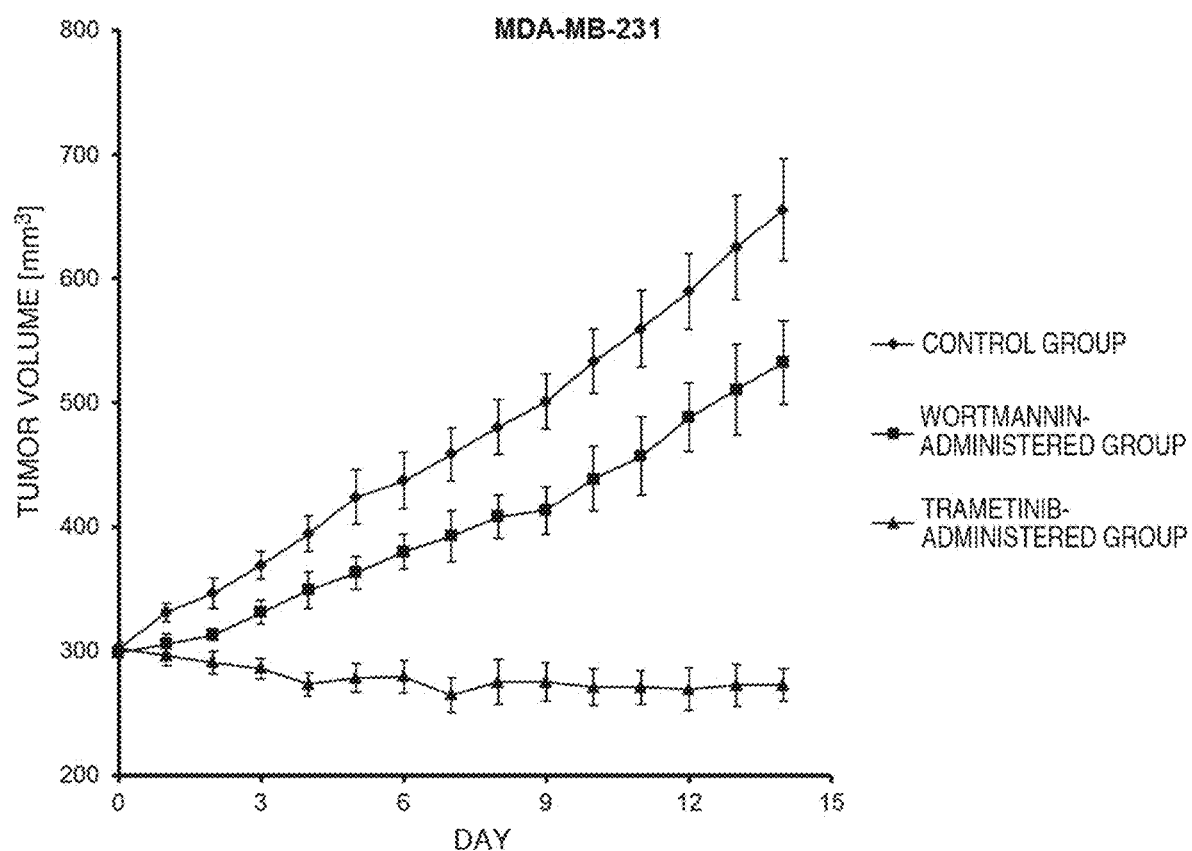

FIG. 33: Suppression of tumor growth by drug administration using tumor-bearing mice prepared from MDA-MB-231

Figure 34:
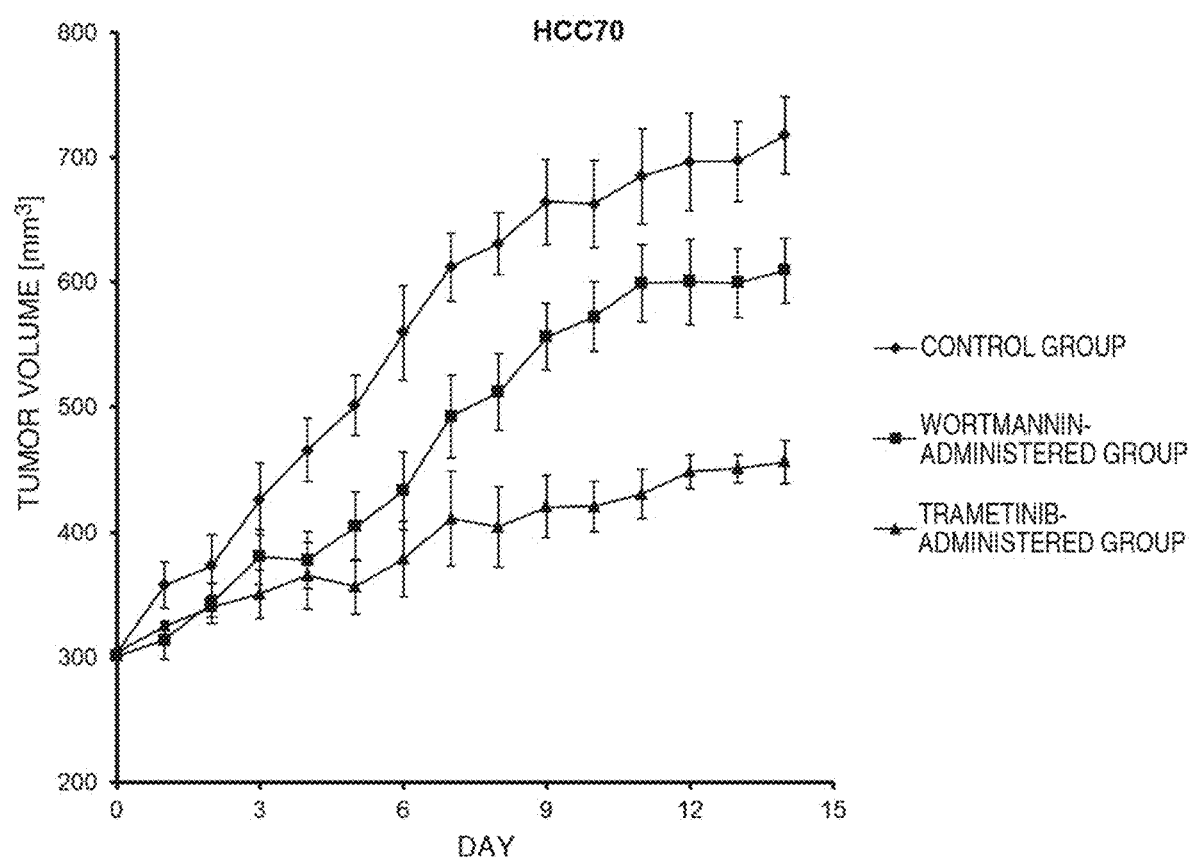

FIG. 34: Suppression of tumor growth by drug administration using tumor-bearing mice prepared from HCC70.

Figure 35:
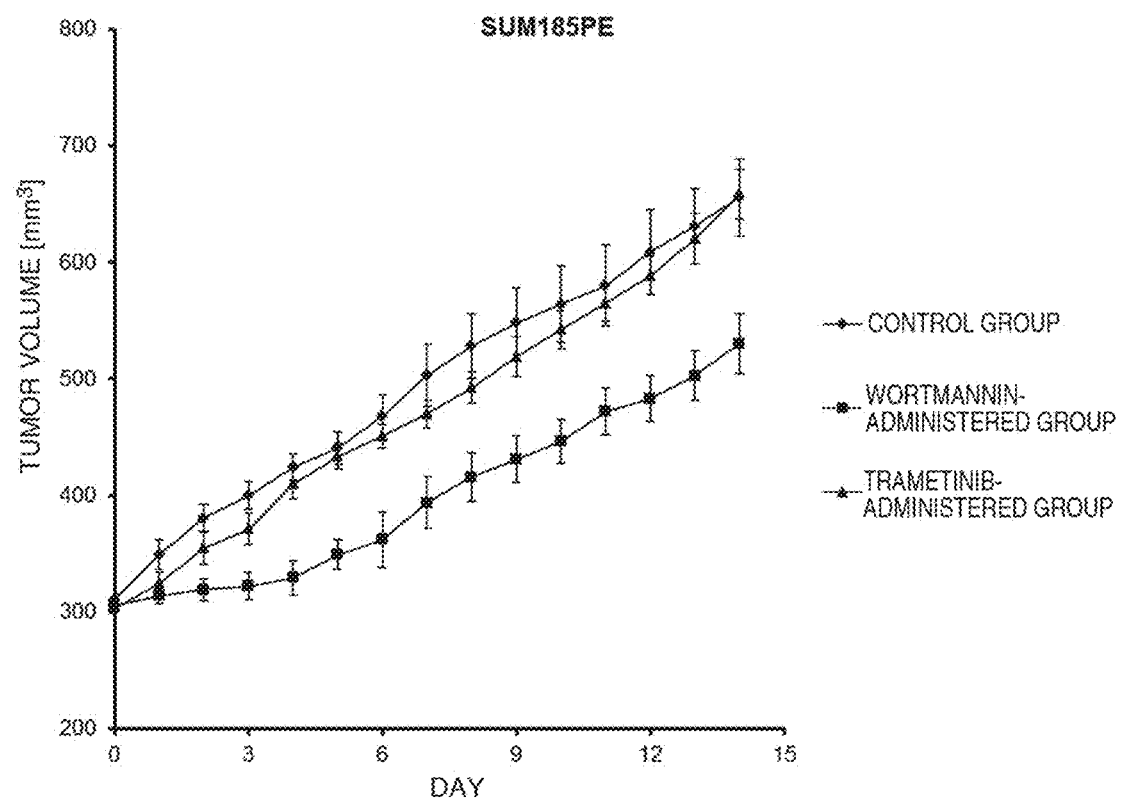

FIG. 35: Suppression of tumor growth by drug administration using tumor-bearing mice prepared from SUM185PE.

DESCRIPTION OF EMBODIMENT

Malignant tumors are tumors which invade surrounding tissues or develop metastasis among cell populations (tumors, benign tumors and malignant tumors) which show autonomous and uncontrolled growth by genetic mutation, and the term malignant tumors is classified into:

1) Carcinoma: malignant tumors derived from epithelial tissues,

2) Sarcoma: malignant tumors derived from non-epithelial tissues, and

3) Others: leukemia, etc.

in pathology, and in the application, "cancer cells" mean carcinoma cells. Examples thereof include, but not limited to, cancer cells such as head and neck cancers (maxillary cancers, (nasopharyngeal, mesopharyngeal and hypopharyngeal) cancers, pharyngeal cancers, tongue cancers, and thyroid cancers), thoracic cancers (breast cancers, and lung cancers (non-small cell lung cancers and small-cell lung cancers)), digestive cancers (esophageal cancers, stomach cancers, duodenal cancers, large intestine cancers (colon cancers and rectal cancers), hepatic cancers (hepatomas and cholangiocellular cancers), gallbladder cancers, bile duct cancers, pancreatic cancers, anal cancers, urinary tract cancers (kidney cancers, ureter cancers, bladder cancers, prostatic cancers, penile cancers and testicular (testicle) cancers), genital cancers (uterine cancers (cervical cancers and uterine body cancers), ovarian cancers, vulvar cancers and vaginal cancers), skin cancers (basal cell cancers and squamous cell cancers).

"Inhibitor sensitivity" means, but not limited to, that cells cause growth inhibition by an inhibitor. As an example, when a cancer diagnosed as an HER2-positive cancer causes growth inhibition and shows good pCR by trastuzumab, an anti-HER2 monoclonal antibody, in actual clinical site by anticancer drug therapy, the cancer can be defined as "inhibitor sensitivity." In addition, when a cancer diagnosed as a luminal type (ER·PgR-positive) cancer causes growth inhibition and shows good pCR by tamoxifen, an antiestrogen drug, in actual clinical site by anticancer drug therapy, the cancer can be defined as "inhibitor sensitivity."

"Inhibitor insensitivity" means, but not limited to, that cells do not cause growth inhibition by an inhibitor. As an example, when a cancer diagnosed as an HER2-negative cancer does not cause growth inhibition and pCR is not improved by trastuzumab, an anti-HER2 monoclonal antibody, in actual clinical site by anticancer drug therapy, the cancer can be defined as "inhibitor insensitivity." In addition, when a cancer diagnosed as a non-luminal type (ER·PgR-negative) cancer does not cause growth inhibition and pCR is not improved by tamoxifen, an antiestrogen drug, in actual clinical site by anticancer drug therapy, the cancer can be defined as "inhibitor insensitivity."

Alternatively, about "inhibitor insensitivity", cell growth inhibition is not caused under the same conditions as when a cancer cell line used in Examples is prescribed to be triple negative breast cancer, under inhibitor-added conditions, which can be also defined as "inhibitor insensitivity."

Additionally, showing a growth inhibition rate of 12.5%, 25% or 50% or more in an inhibitor concentration of 100 nM, 1 μM or 10 μM can be defined as "inhibitor sensitivity."

Contrarily, showing a growth inhibition rate of less than 12.5%, 25% or 50% in an inhibitor concentration of 100 nM, 1 µM or 10 µM can be defined as "inhibitor insensitivity."

More preferably, showing a growth inhibition rate of 12.5% or more in a drug concentration of 100 nM, a growth inhibition rate of 25% or more in a drug concentration of 1 µM, or a growth inhibition rate of 50% or more in a drug concentration of 10 µM can be defined as "inhibitor sensitivity"; contrarily, showing a growth inhibition rate of less than 12.5% in a drug concentration of 100 nM, a growth inhibition rate of less than 25% in a drug concentration of 1 µM, or a growth inhibition rate of less than 50% in a drug concentration of 10 µM can be also defined as "inhibitor insensitivity."

The "enzyme activity of PI3K and MEK" means activity that each kinase "phosphorylates" a target thereof. The activity has the same meaning as activity which decomposes ATP, a supply source of phosphoric acid for "phosphorylation," into ADP and phosphoric acid.

The "effect prediction of a PI3K inhibitor or an MEK inhibitor" means to predict the effect of the inhibitor suppressing the growth of cancer cells, and preferably means to predict the effect of the inhibitor effectively functioning as an anticancer drug in a living body.

The "tissue sample" means a tissue isolated from human or non-human animals. The "tissue sample" can be for example cryopreserved after isolation.

The "biopsy" means to collect a part of pathological tissue with e.g. a surgical knife and a needle for observation by e.g. a microscope in a diagnosis. Preferably, it is desired that the biopsy be carried out before administering a PI3K inhibitor and an MEK inhibitor. In the case of breast cancer, a tissue is collected from the breast of a patient by "excision biopsy" (the removal of an entire tissue lump); "incision biopsy" (the removal of a portion); "core biopsy" (the removal of a part of tissue with a thick needle); or "fine needle aspiration (FNA) biopsy" (the removal of a tissue or body fluid with a thin needle).

The "anti-PI3K antibody" and "anti-MEK antibody" in a "kit" can exist in the liquid state, and can be dried to exist in the solid state, and moreover can be directly bound to a solid layer including beads and plates; and can be indirectly fixed via Protein A, G and L and fused proteins thereof or antibodies recognizing the "anti-PI3K antibody" and "anti-MEK antibody" (e.g. an antibody recognizing a mouse IgG when the "anti-PI3K antibody" and "anti-MEK antibody" are a mouse IgG antibody).

In a "kit," each "measurement reagent" can exist in the solution state in which reagent components are dissolved, and can be in the dry solid state. When a "measurement reagent" is in the solid state, a "kit" can include a "solvent" to dissolve the "measurement reagent."

The "anti-PI3K antibody" indicates an antibody which specifically recognizes and binds to PI3K having natural activity. It is preferred that binding not inhibit the activity of PI3K. The "anti-PI3K antibody" can be antibodies which recognize subunits of PI3K, PI3K Class I (IA, IB), Class II and Class III, and can be a combination of those specific antibodies. The "anti-PI3K antibody" is desirably an antibody which recognizes p110α subunit of Class IA.

The "anti-MEK antibody" indicates an antibody which specifically recognizes and binds to MEK having naturally-derived activity. The "anti-MEK antibody" can be antibodies which recognize MEK1 to 7, and can be a combination of those specific antibodies. The "anti-MEK antibody" can be antibodies which specifically recognize MEK1 and MEK2 involved in the activity of ERK1/2, or a combination of an antibody which specifically recognizes MEK1 and an antibody which specifically recognizes MEK2.

The "antibodies" can be full-length (IgG, IgA, IgM, IgD, and IgE) immunoglobulins, and fragments including an antigen-binding recognizing site (i.e. fragment antibodies (such as Fab, Fab', F(ab')2). In addition, the "antibodies" can be those derived from mammals such as human, mouse, rat, goat, horse and camel, and those derived from fish (including shark) and bird (chicken).

The "reference standard" indicates cells insensitive to both a PI3K inhibitor and an MEK inhibitor, or cells sensitive to both a PI3K inhibitor and an MEK inhibitor; or a tissue including the cells.

The "PI3K activity/MEK activity ratio of a reference standard" can be "the PI3K activity/MEK activity ratio" calculated from a cell tissue derived from a specimen, or "the PI3K activity/MEK activity ratio" calculated from tissue cells derived from a plurality of patients or healthy individuals, or can be "the PI3K activity/MEK activity ratio" calculated from one or more types of cultured cells. In the case of breast cancer, the "PI3K activity/MEK activity ratio of a reference standard" can be "the PI3K activity/MEK activity ratio" calculated from a cell tissue removed from the opposite breast which does not develop cancer.

The "patients" can be mammals, and can be "human" or "non-human mammals."

EXAMPLES

The present invention will now be described in more detail by way of Examples and Comparative Examples below. It should be noted, however, that the present invention is not limited to these Examples.

Example 1

Classification of Cell Lines Sensitive to an MEK Inhibitor and Sensitive to a PI3K Inhibitor by Cell Growth Test Using Cultured Cells 1. Method Cultured cells were treated with a MEK inhibitor and a PI3K inhibitor in various concentrations, and cell lines sensitive to MEK and PI3K were classified by calculating a cell growth inhibition rate. The culture method and analysis method are as follows.

Established Cells and Cell Culture

Thirteen types of cells used in the present study, HCC38 (BL1), MDA-MB-231 (MSL), DU4475 (IM), HCC1187 (IM), HCC1143 (BL1), HCC1395 (LAR), HCC1937 (BL1), MDA-MB-453 (LAR), HCC70 (BL2), HS578T (MSL), MDA-MB-157 (MSL) and MDA-MB-468 (BL1), were obtained from American type culture collection (ATCC), and SUM185PE (LAR) was obtained from ASTERAND BIOSCIENCE. All the cells belong to triple negative breast cancer (TNBC), and it is known which of six types (BL1, BL2, M, MSL, IM and LAR) these belong to by an existing classification method.

All the cells were cultured in a medium designated from a source of supply, and 2 mM L-glutamine and 10% fetal bovine serum (FBS) were supplemented.

Drug Sensitivity Assay (Cell Growth Test)

Each type of cells was seeded in a 96 well titer plate at $1 \times 10^4$ cells/well, and trametinib, an MEK inhibitor (Medchem Express; 0.08, 0.16, 0.31, 0.63, 1.25, 2.5, 5, 10 and 20 µM), and wortmannin, a PI3K inhibitor (Wako Pure Chemical Industries, Ltd.; 0.08, 0.16, 0.31, 0.63, 1.25, 2.5, 5, 10 and 20 µM) were dissolved in Dimethyl Sulfoxide [DMSO]

(Wako Pure Chemical Industries, Ltd.) in various concentrations and treated. In addition, the effect on cell growth was examined at 72 hours after the inhibitor by sulforhodamine B assay (manufactured by SIGMA-ALDRICH), and 50 μL of sulforhodamine B solution was added to each well and cells were left at room temperature for an hour for staining. The staining degree of metabolically survival cells was examined by monitoring absorbance at a wavelength of 565 nm using a microtiter plate. The absorbance of cells which were not treated with trametinib and wortmannin (treated with DMSO) was used as a control and defined as 100% to calculate a cell growth inhibition rate.

2A. Results

The results are shown in FIG. 1A. The cell lines were classified into 4 types, cell lines sensitive to wortmannin (hereinafter, PA), cell lines sensitive to trametinib (hereinafter, MA), cell lines resistant to wortmannin and trametinib (hereinafter, R), and others (hereinafter, S). In the classification, first the inhibition rate of each drug was calculated in a concentration of 1 μM, and the inhibition rate (%) by trametinib and the inhibition rate (%) by wortmannin were plotted on the X axis and Y axis respectively on a graph. Using a 25% growth inhibition rate as an index of the inhibitory effect of a drug, cells were classified into 4 types by grid analysis.

By this method, HCC38 (BL1), MDA-MB-231 (MSL), DU4475 (IM), HCC1187 (IM) and HCC1143 (BL1); HCC1395 (LAR), HCC1937 (BL1), HS578T (MSL) and MDA-MB-157 (MSL); MDA-MB-453 (LAR) and HCC70 (BL2); and MDA-MB-468 (BL1) and SUM185PE (LAR) could be classified as MA, R, S, and PA, respectively.

This result was a result which cannot be expected by the existing classification method.

2B. Results

The results are shown in FIG. 1B. The cell lines were classified into 4 types, cell lines sensitive to wortmannin (hereinafter, PA), cell lines sensitive to trametinib (hereinafter, MA), cell lines resistant to wortmannin and trametinib (hereinafter, R), and others (hereinafter, S). In the classification, first the inhibition rate of each drug was calculated in a concentration of 100 nM, and the inhibition rate (%) by trametinib and the inhibition rate (%) by wortmannin were plotted on the X axis and Y axis respectively on a graph. Using a 12.5% growth inhibition rate as an index of the inhibitory effect of a drug, cells were classified into 4 types by grid analysis.

By this method, HCC38 (BL1), MDA-MB-231 (MSL), DU4475 (IM), HCC1187 (IM) and HCC1143 (BL1); HCC1395 (LAR), HCC1937 (BL1), HS578T (MSL) and MDA-MB-157 (MSL); MDA-MB-453 (LAR) and HCC70 (BL2); and MDA-MB-468 (BL1) and SUM185PE (LAR) could be classified as MA, R, S, and PA, respectively.

This result was a result which cannot be expected by the existing classification method.

2C. Results

The results are shown in FIG. 1C. The cell lines were classified into 4 types, cell lines sensitive to wortmannin (hereinafter, PA), cell lines sensitive to trametinib (hereinafter, MA), cell lines resistant to wortmannin and trametinib (hereinafter, R), and others (hereinafter, S). In the classification, first the inhibition rate of each drug was calculated in a concentration of 10 μM, and the inhibition rate (%) by trametinib and the inhibition rate (%) by wortmannin were plotted on the X axis and Y axis respectively on a graph. Using a 50% growth inhibition rate as an index of the inhibitive effect of a drug, cells were classified into 4 types by grid analysis.

By this method, HCC38 (BL1), MDA-MB-231 (MSL), DU4475 (IM), HCC1187 (IM) and HCC1143 (BL1); HCC1395 (LAR), HCC1937 (BL1), HS578T (MSL) and MDA-MB-157 (MSL); MDA-MB-453 (LAR) and HCC70 (BL2); and MDA-MB-468 (BL1) and SUM185PE (LAR) could be classified as MA, R, S, and PA, respectively.

This result was a result which cannot be expected by the existing classification method.

As described above, cell lines can be classified into drug sensitivity and drug insensitivity by the above grid analysis with extremely good reproducibility without the numerical limitations of drug concentrations and growth inhibition rates.

Example 2

Activity Measurement of Kinases in a Cultured Cell Lysate

1. Method

A cell lysate was prepared from cultured cells, a target kinase was captured by using an antibody specific to each kinase, and measurement was then made using high performance liquid chromatography [HPLC]. The method for preparing a measurement sample and the measurement method will be described below.

Preparation of a Cell Lysate for Kinase Analysis

A lysate of established cells used for kinase analysis was prepared as follows. Cells were cultured in a predetermined medium with 10% FBS (fetal bovine serum). Cells were collected after culturing up to about $1 \times 10^7$ cells, and washed once with PBS. Next, cells were lysed with a lysis buffer (0.1% NP-40, 50 mM tris-HCl [pH 7.4], 150 mM NaCl) by 20 times injection with a 24 G needle. In order to remove non-lysed material, centrifugation was carried out at 15000 rpm for 5 minutes to obtain a cell lysate.

Capture and Activity Measurement of MEK in a Cell Lysate

The MEK activity was measured using HPLC. Specifically, the amount of ADP, a product generated by a kinase reaction, was measured, and the concentration was converted into kinase activity. A cell lysate was prepared as described in the previous section. MEK molecules were selectively precipitated from 200 μL of cell lysate with 4 μg of corresponding antibody (anti-MEK1/MEK2; Santa Cruz Biotechnology) and 100 μL of protein G beads (Life technologies) at 4° C. for 2 hours. After washing twice with a wash buffer 1 (0.1% TX-100, 50 mM tris-HCl [pH 7.4], 150 mM NaCl), followed by twice with a wash buffer 2 (50 mM tris-HCl [pH 7.4], 150 mM NaCl), 100 μL of substrate mixture including 1 μg of protein substrate (unactive-ERK; Signalchem), 2 mM adenosine triphosphate (ATP) (Sigma), 70 mM tris-HCl (pH 8.5), and 7 mM magnesium chloride was added to beads, and the obtained mixture was incubated at 37° C. for 2 hours with continuous shaking. After completion of the reaction, the substrate-reaction mixed liquid was applied to HPLC and the amount of ADP in the reaction mixed liquid was measured and converted into activity. It should be noted that the amount of ADP was calculated using a calibration curve created in advance using ADP with a known concentration. In addition, 1 unit (U) was prescribed as an enzyme amount for 1 pmol ADP generated at 37° C. for a minute.

Method for Measuring Activity

The measurement conditions will be described below.

AgilentTechnologies 1220 Infinity LC, Tosoh TSKgel ODS-100V 5 μM 4.6×150 mm, Eluent A: Acetonitrile with 0.1% Trifluoro acetic acid (Fluka), Eluent B: Water with 0.1% Trifluoro acetic acid (Fluka), Flow rate 0.5 mL/min, Wavelength: 254 nm.

Activity Measurement of PI3K

As is the case with MEK, PI3K activity was also measured using HPLC. A cell lysate was prepared in the same manner as in the activity measurement of MEK. PI3K molecules were selectively precipitated from 200 μL of cell lysate with 12 μg of corresponding antibody (anti-PI3K 110a; Santa Cruz Biotechnology) and 150 μL of protein G beads (Life technologies) at 4° C. for 2 hours. After washing twice with a wash buffer 1 (0.1% TX-100, 50 mM tris-HCl [pH 7.4], 150 mM NaCl), followed by twice with a wash buffer 2 (50 mM tris-HCl [pH 7.4], 150 mM NaCl), 100 μL of substrate mixture including 50 nM substrate (L-a-Phosphatidylinositol sodium salt; Sigma), 2 mM adenosine triphosphate (ATP) (Sigma), 70 mM tris-HCl (pH 7.5), and 7 mM magnesium chloride was added to beads, and the obtained mixture was incubated at 37° C. for 2 hours with continuous shaking. After completion of the reaction a reaction mixed liquid was applied to HPLC and the amount of ADP in the reaction liquid was measured and converted into activity. It should be noted that the amount of ADP was calculated using a calibration curve created in advance using ADP with a known concentration. In addition, 1 unit (U) was prescribed as an enzyme amount for 1 pmol ADP generated at 37° C. for a minute. The measurement method is the same as above.

2. Results

As shown in [Table 1], cell lines showed different kinase activity values.

TABLE 1

| | MEK ACTIVITY VALUE [U] | PI3K ACTIVITY VALUE [U] |
|---|---|---|
| MDA-MB-453 | 25.6 | 7.03 |
| HCC1937 | 8.65 | 2.09 |
| HCC1187 | 12.85 | 0.81 |
| MDA-MB-468 | 3.87 | 8.90 |
| HS578T | 3.53 | 5.08 |
| MDA-MB-157 | 2.84 | 5.50 |
| HCC70 | 2.53 | 3.24 |
| MDA-MB-231 | 13.79 | 1.49 |
| SUM185PE | 12.54 | 32.27 |
| HCC1395 | 40.76 | 3.75 |
| HCC38 | 23.83 | 0.24 |

TABLE 1-continued

| | MEK ACTIVITY VALUE [U] | PI3K ACTIVITY VALUE [U] |
|---|---|---|
| HCC1143 | 18.62 | 1.57 |
| DU4475 | 28.60 | 1.39 |

Example 3

Measurement of the Expression Level and the Phosphorylation Level of Kinases in a Cultured Cell Lysate by Western Blotting 1. Method The expression levels were measured from a cell lysate obtained in the above-described method by Western blotting. In addition, the absorbance at 280 nm was measured by a spectrophotometer to normalize the number of cells. The method will be described below.

Measurement of the Expression Levels of MEK and PI3K, the Expression Levels of Phosphorylation, the Expression Level of Phosphorylated ERK and the Expression Level of Phosphorylated AKT by Western Blotting A lysate of established cells used for the analysis of expression levels and phosphorylation levels was also prepared in the same manner as in the activity measurement. For Western blotting, a lysate of established cells was subjected to sodium dodecylsulfate-polyacrylamide gel electrophoresis, and the gel was transferred to a nitrocellulose membrane. The membrane was incubated at room temperature for an hour (or at 4° C. overnight) with polyclonal anti-MEK1/2 antibody (Cell signaling; 1:1000), polyclonal anti-Phospho-MEK1/2 antibody (Ser217/221) (Cell signaling; 1:1000), polyclonal anti-PI3K p110α antibody (Cell signaling; 1:1000), polyclonal anti-Phospho-PI3K p85 (Tyr458)/p55 (Try199) antibody (Cell signaling; 1:1000), polyclonal anti-Phospho-ERK1/2 antibody (Thr202/Tyr204) (Cell signaling; 1:1000), polyclonal anti-Phospho-AKT antibody (Thr308) (Cell signaling; 1:1000), and then incubated with a horseradish peroxidase-binding antibody. The result was enhanced in a chemiluminescent detection system for visualization. A calibration curve was created using recombinant MEK and PI3K, and the levels of MEK, phosphorylated MEK, PI3K and phosphorylated PI3K were calculated.

2. Results

As shown in [Table 2], cell lines showed different expression levels and phosphorylation levels of kinases.

TABLE 2

| | EXPRESSION LEVEL OF MEK [ng] | EXPRESSION LEVEL OF PI3K [ng] | EXPRESSION LEVEL OF PHOSPYORYLATED MEK [U] | EXPRESSION LEVEL OF PHOSPYORYLATED PI3K [U] | EXPRESSION LEVEL OF PHOSPHORYLATED ERK [U] | EXPRESSION LEVEL OF PHOSPHORYLATED AKT [U] |
|---|---|---|---|---|---|---|
| MDA-MB-453 | 9.71 | 11.01 | 2.55 | 32.47 | 1.55 | 6.47 |
| HCC1937 | 0.47 | 3.19 | 1.59 | 6.10 | 1.46 | 4.26 |
| HCC1187 | 2.21 | 5.97 | 1.84 | 57.36 | 1.49 | 5.44 |
| MDA-MB-468 | 14.02 | 8.45 | 11.52 | 181.39 | 2.04 | 5.28 |
| HS578T | 2.61 | 2.05 | 2.30 | 78.03 | 1.05 | 4.51 |
| MDA-MB-157 | 12.11 | 2.27 | 2.07 | 545.10 | 1.27 | 4.43 |
| HCC70 | 2.53 | 2.66 | 2.71 | 5.74 | 0.95 | 4.87 |
| MDA-MB-231 | 1.01 | 4.66 | 12.68 | 66.2 | 0.93 | 5.06 |
| SUM185PE | 3.11 | 8.26 | 2.60 | 118.6 | 1.02 | 6.05 |
| HCC1395 | 2.90 | 3.70 | 3.80 | 181.4 | 1.20 | 18.20 |
| HCC38 | 6.80 | 8.80 | 0.70 | 99.3 | 1.90 | 3.80 |
| HCC1143 | 8.90 | 19.20 | 0.80 | 20.00 | 1.00 | 1.40 |
| DU4475 | 10.30 | 2.30 | 15.80 | 78.00 | 6.20 | 4.50 |

Example 4

Measurement of LDH Activity and A280 in a Cell Lysate
1. Method

Using N-Assay LDH (NITTOBO MEDICAL CO., LTD.) as a reagent and HITACHI 7180 automatic analyzer as a measuring instrument, 4 µL of sample and 160 µL of first reagent were mixed in a cell lysate obtained in the above-described method at 37° C. for 5 minutes, and to the obtained liquid, 40 µL of second reagent was then added to cause a chromogenic reaction at the same temperature for 5 minutes. Changes in absorbance per minute after the initiation of the chromogenic reaction were measured at a main wavelength of 340 nm and a secondary wavelength of 405 nm. The LDH activity [U] was calculated from the amount of absorbance change using a reference solution with a known concentration.

In addition, the absorbance at 280 nm of the same lysate was measured using Pharmacia Biotech Ultraspec 3000 spectrophotometer, and the obtained absorbance was converted using ABS 1.0=1.0 mg/mL.

The above two types of value were used to normalize the number of cells.

2. Results

As shown in [Table 3], the LDH activity and the total amount of protein of each cell line were obtained.

TABLE 3

|  | LDH ACTIVITY VALUE [U] | TOTAL AMOUNT OF PROTEIN [mg/mL] |
|---|---|---|
| MDA-MB-453 | 5340 | 6.72 |
| HCC1937 | 660 | 3.56 |
| HCC1187 | 2780 | 7.68 |
| MDA-MB-468 | 5820 | 8.02 |
| HS578T | 6740 | 6.52 |
| MDA-MB-157 | 3840 | 6.06 |
| HCC70 | 1300 | 4.72 |
| MDA-MB-231 | 11640 | 8.56 |
| SUM185PE | 4140 | 7.74 |
| HCC1395 | 10435 | 14.16 |
| HCC38 | 23125 | 14.38 |
| HCC1143 | 18385 | 18.80 |
| DU4475 | 8255 | 13.80 |

Example 5

Construction of Determination Parameters for Cell Lines Sensitive to an MEK Inhibitor and Cell Lines Sensitive to a PI3K Inhibitor
1. Method Using 8 values calculated above (Examples 2 to 4) related to protein kinases, i.e. I: MEK activity, II: PI3K activity, III: the expression level of MEK, IV: the phosphorylation level of MEK, V: the expression level of PI3K, VI: the phosphorylation level of PI3K, VII: LDH activity, and VIII: the total amount of protein, parameters to predict the drug sensitivity of cell lines classified above were constructed.

For the analysis, HCC38 (BL1), MDA-MB-231 (MSL), DU4475 (IM), HCC1187 (IM), HCC1143 (BL1), HCC1395 (LAR), HCC1937 (BL1), HS578T (MSL), MDA-MB-157 (MSL), MDA-MB-453 (LAR), HCC70 (BL2), MDA-MB-468 (BL1), and SUM185PE (LAR) were defined as cell line 1, cell line 2, cell line 3, cell line 4, cell line 5, cell line 6, cell line 7, cell line 8, cell line 9, cell line 10, cell line 11, cell line 12 and cell line 13, respectively.

2. Results

As a result of diligent investigation, cell lines sensitive to two types of inhibitor can be predicted at a high probability using a parameter, "PI3K activity/MEK activity." Specifically, cell lines sensitive to a PI3K inhibitor (PA) are in a region in which the values of "PI3K activity/MEK activity" are high i.e. a region in which PI3K activity is much higher than MEK activity. Contrarily to the above, cell lines sensitive to an MEK inhibitor (MA) are in a region in which the values of "PI3K activity/MEK activity" are low i.e. a region in which MEK activity is much higher than PI3K activity (FIG. 2).

Contrarily to this, when using similar parameters, "the expression level of PI3K/the expression level of MEK" (Comparative Example 1: FIG. 3), "the expression level of phosphorylated PI3K/the expression level of phosphorylated MEK" (Comparative Example 2: FIG. 4) and "the expression level of phosphorylated AKT/the expression level of phosphorylated ERK," which are reaction products, (Comparative Example 3: FIG. 5), such tendency could not be observed, and prediction could not be made. The results showed that it was effective to measure activity instead of expression levels and phosphorylation levels.

Example 6

Determination of Cell Lines Sensitive to an MEK Inhibitor and Cell Lines Sensitive to a PI3K Inhibitor by Grid Analysis
1. Method As is the case in Example 5, parameters calculated using 8 values, i.e. I: MEK activity, II: PI3K activity, III: the expression level of MEK, IV: the phosphorylation level of MEK, V: the expression level of PI3K, VI: the phosphorylation level of PI3K, VII: LDH activity, and VIII: the total amount of protein were plotted on a 2-axis graph, and verification including a cutoff condition was conducted. In addition, values were plotted on a graph using ■ for MA, ▲ for PA and ♦ for other cell lines.

As evaluation items for grid analysis, 5 items, sensitivity, specificity, positive predictive value, negative predictive value and accuracy, were calculated.

The sensitivity is defined as "a probability that a cell line which should be judged to be sensitive is correctly determined to be sensitive" in this verification. As an example, when two cell lines sensitive to an MEK inhibitor (MA) are contained in all cell lines used in an analysis and one of the sensitive cell lines is plotted in a region determined to be sensitive to an MEK inhibitor as a result of the analysis, the sensitivity is ½=50%.

The specificity is defined as "a probability that a cell line which should be judged to be insensitive is correctly determined to be insensitive" in this verification. As an example, when 8 cell lines insensitive to an MEK inhibitor are contained in all cell lines used in an analysis and 4 insensitive cell lines are plotted in a region determined to be insensitive to an MEK inhibitor as a result of the analysis, the specificity is 4/8=50%.

The positive predictive value is defined as "a probability of true sensitivity when sensitivity is determined" in this verification. As an example, when 2 cell lines are plotted in a region determined to be sensitive to an MEK inhibitor and one of the cell lines is sensitive to an MEK inhibitor as a result of an analysis, the positive predictive value is ½=50%.

The negative predictive value is defined as "a probability of true insensitivity when insensitivity is determined" in this verification. As an example, when 6 cell lines are plotted in a region determined to be insensitive to an MEK inhibitor and five of the cell lines are insensitive to an MEK inhibitor as a result of an analysis, the negative predictive value is 5/6=83%.

The accuracy is defined as "the percentage of true sensitive cell lines and true insensitive cell lines to the whole" in this verification. As an example, in a case where the total number of cell lines used in an analysis is 10 and there are two cell lines sensitive to an MEK inhibitor and 8 cell lines insensitive to an MEK inhibitor among them, when one of the cell lines sensitive to an MEK inhibitor is determined to be sensitive (true positive), the remaining one is determined to be insensitive (false-negative), two of the cell lines insensitive to an MEK inhibitor are determined to be sensitive (false-positive) and the remaining 6 cell lines (true negative) were determined to be insensitive as a result of the analysis, in this case, the accuracy is (1+6)/(1+2+1+6)=70%.

2. Results

As a result of various investigations, grid analysis was carried out by combinations of a few types of parameters (Tables 4 to 9). Among these, the following 6 types are the parameters which are able to predict drug sensitivity of cell lines (FIGS. 6, 10, 14, 18, 22 and 26):

1) X: PI3K activity/LDH activity, Y: MEK activity/LDH activity (FIG. 6),
2) X: PI3K activity/MEK activity, Y: PI3K activity/LDH activity (FIG. 10),
3) X: PI3K activity/MEK activity, Y: MEK activity/LDH activity (FIG. 14),
4) X: PI3K activity/the total amount of protein, Y: MEK activity/the total amount of protein (FIG. 18),
5) X: PI3K activity/MEK activity, Y: PI3K activity/the total amount of protein (FIG. 22), and
6) X: PI3K activity/MEK activity, Y: MEK activity/the total amount of protein (FIG. 26).

Contrarily, when using the expression levels (FIGS. 7, 11, 15, 19, 23 and 27), the phosphorylation levels (FIGS. 8, 12, 16, 20, 24 and 28), or the phosphorylation levels of a substrate (FIGS. 9, 13, 17, 21, 25 and 29) instead of activity values, sensitivity could not be predicted (Comparative Examples 4 to 21).

1) Parameter Comparison

TABLE 4

|  |  | GRID ANALYSIS BY 1) | | | |
|---|---|---|---|---|---|
|  |  | ACTIVITY | EXPRESSION LEVEL | PHOSPHORYLATION LEVEL | PHOSPHORYLATION LEVEL OF SUBSTRATE |
| MA | SENSITIVITY | 40% | 0% | 40% | 20% |
|  | SPECIFICITY | 88% | 75% | 100% | 100% |
|  | POSITIVE PREDICTIVE VALUE | 67% | 0% | 100% | 100% |
|  | NEGATIVE PREDICTIVE VALUE | 80% | 45% | 73% | 67% |
|  | ACCURACY | 77% | 38% | 77% | 69% |
| PA | SENSITIVITY | 100% | 0% | 0% | 0% |
|  | SPECIFICITY | 91% | 82% | 82% | 100% |
|  | POSITIVE PREDICTIVE VALUE | 67% | 0% | 0% | 0% |
|  | NEGATIVE PREDICTIVE VALUE | 100% | 82% | 82% | 83% |
|  | ACCURACY | 92% | 69% | 69% | 77% |

2) Parameter Comparison

TABLE 5

|  |  | GRID ANALYSIS BY 2) | | | |
|---|---|---|---|---|---|
|  |  | ACTIVITY | EXPRESSION LEVEL | PHOSPHORYLATION LEVEL | PHOSPHORYLATION LEVEL OF SUBSTRATE |
| MA | SENSITIVITY | 100% | 60% | 60% | 100% |
|  | SPECIFICITY | 75% | 50% | 63% | 63% |
|  | POSITIVE PREDICTIVE VALUE | 71% | 43% | 38% | 63% |
|  | NEGATIVE PREDICTIVE VALUE | 100% | 67% | 60% | 100% |
|  | ACCURACY | 85% | 54% | 46% | 77% |
| PA | SENSITIVITY | 100% | 0% | 0% | 0% |
|  | SPECIFICITY | 100% | 82% | 73% | 73% |
|  | POSITIVE PREDICTIVE VALUE | 67% | 0% | 0% | 0% |
|  | NEGATIVE PREDICTIVE VALUE | 91% | 82% | 80% | 80% |
|  | ACCURACY | 92% | 69% | 62% | 77% |

3) Parameter Comparison

TABLE 6

|  |  | GRID ANALYSIS BY 3) | | | |
|---|---|---|---|---|---|
|  |  | ACTIVITY | EXPRESSION LEVEL | PHOSPHORYLATION LEVEL | PHOSPHORYLATION LEVEL OF SUBSTRATE |
| MA | SENSITIVITY | 40% | 0% | 20% | 20% |
|  | SPECIFICITY | 63% | 75% | 100% | 100% |
|  | POSITIVE PREDICTIVE VALUE | 100% | 0% | 100% | 100% |

TABLE 6-continued

|  |  | GRID ANALYSIS BY 3) | | | |
|---|---|---|---|---|---|
|  |  | ACTIVITY | EXPRESSION LEVEL | PHOSPHORYLATION LEVEL | PHOSPHORYLATION LEVEL OF SUBSTRATE |
|  | NEGATIVE PREDICTIVE VALUE | 73% | 82% | 67% | 64% |
|  | ACCURACY | 77% | 69% | 54% | 62% |
| PA | SENSITIVITY | 100% | 50% | 0% | 100% |
|  | SPECIFICITY | 64% | 45% | 45% | 55% |
|  | POSITIVE PREDICTIVE VALUE | 33% | 14% | 0% | 33% |
|  | NEGATIVE PREDICTIVE VALUE | 100% | 83% | 71% | 100% |
|  | ACCURACY | 54% | 46% | 38% | 69% |

4) Parameter Comparison

TABLE 7

|  |  | GRID ANALYSIS BY 4) | | | |
|---|---|---|---|---|---|
|  |  | ACTIVITY | EXPRESSION LEVEL | PHOSPHORYLATION LEVEL | PHOSPHORYLATION LEVEL OF SUBSTRATE |
| MA | SENSITIVITY | 40% | 20% | 40% | 40% |
|  | SPECIFICITY | 88% | 88% | 88% | 88% |
|  | POSITIVE PREDICTIVE VALUE | 67% | 50% | 40% | 67% |
|  | NEGATIVE PREDICTIVE VALUE | 80% | 64% | 70% | 90% |
|  | ACCURACY | 92% | 62% | 69% | 85% |
| PA | SENSITIVITY | 100% | 50% | 0% | 0% |
|  | SPECIFICITY | 100% | 88% | 73% | 73% |
|  | POSITIVE PREDICTIVE VALUE | 100% | 50% | 0% | 0% |
|  | NEGATIVE PREDICTIVE VALUE | 100% | 91% | 80% | 80% |
|  | ACCURACY | 100% | 85% | 62% | 62% |

5) Parameter Comparison

TABLE 8

|  |  | GRID ANALYSIS BY 5) | | | |
|---|---|---|---|---|---|
|  |  | ACTIVITY | EXPRESSION LEVEL | PHOSPHORYLATION LEVEL | PHOSPHORYLATION LEVEL OF SUBSTRATE |
| MA | SENSITIVITY | 100% | 40% | 80% | 100% |
|  | SPECIFICITY | 63% | 50% | 50% | 75% |
|  | POSITIVE PREDICTIVE VALUE | 63% | 33% | 50% | 71% |
|  | NEGATIVE PREDICTIVE VALUE | 100% | 57% | 80% | 100% |
|  | ACCURACY | 77% | 46% | 62% | 77% |
| PA | SENSITIVITY | 100% | 50% | 0% | 0% |
|  | SPECIFICITY | 91% | 91% | 73% | 75% |
|  | POSITIVE PREDICTIVE VALUE | 67% | 50% | 0% | 0% |
|  | NEGATIVE PREDICTIVE VALUE | 100% | 91% | 80% | 82% |
|  | ACCURACY | 92% | 85% | 62% | 69% |

6) Parameter Comparison

TABLE 9

|  |  | GRID ANALYSIS BY 6) | | | |
|---|---|---|---|---|---|
|  |  | ACTIVITY | EXPRESSION LEVEL | PHOSPHORYLATION LEVEL | PHOSPHORYLATION LEVEL OF SUBSTRATE |
| MA | SENSITIVITY | 40% | 20% | 20% | 40% |
|  | SPECIFICITY | 100% | 75% | 88% | 100% |
|  | POSITIVE PREDICTIVE VALUE | 100% | 33% | 40% | 100% |
|  | NEGATIVE PREDICTIVE VALUE | 73% | 60% | 64% | 73% |
|  | ACCURACY | 77% | 54% | 62% | 77% |
| PA | SENSITIVITY | 100% | 50% | 0% | 50% |
|  | SPECIFICITY | 38% | 36% | 45% | 45% |
|  | POSITIVE PREDICTIVE VALUE | 100% | 13% | 0% | 14% |
|  | NEGATIVE PREDICTIVE VALUE | 73% | 80% | 71% | 83% |
|  | ACCURACY | 77% | 38% | 38% | 46% |

Example 7

Activity Measurement of Kinases in a Cultured Cell Lysate by a Kit for the Activity Measurement of Kinases Having a Chemiluminescent Method as a Measurement Principle 1. Method Correlation with a control method (HPLC method: Example 2) was confirmed.

Samples

Sixteen types of breast cancer cell lines were used. Specifically, the sixteen types are HCC38, MDA-MB-231, DU4475, HCC1187, HCC1143, HCC1395, HCC1937, HS578T, MDA-MB-157, MDA-MB-453, HCC70, MDA-MB-468, SUM185PE, BT20, BT549 and HCC1806.

First Reagent

| | |
|---|---|
| Tris-HCl pH 7.5 (SIGMA) | 100 mM |
| MgCl2 (Wako Pure Chemical Industries, Ltd.) | 10 mM |
| EDTA·2Na (DOJINDO LABORATORIES) | 5 mM |
| NaF (Wako Pure Chemical Industries, Ltd.) (phosphatase inhibitor) | 50 mM |
| Na3VO4 (Wako Pure Chemical Industries, Ltd.) (phosphatase inhibitor) | 1 mM |
| Protease inhibitor mixture (NACALAI TESQUE, INC.) | 1% |
| NP-40 (NACALAI TESQUE, INC.) | 0.1% |

Second Reagent

| | |
|---|---|
| 1) For measuring MEK | |
| Dynabeads Protein G (Life technologies) | 15 mg/mL |
| anti-MEK1 antibody (IgG) (Santa Cruz Biotechnology) | 20 μg/mL |
| anti-MEK2 antibody (IgG) (Santa Cruz Biotechnology) | 20 μg/mL |
| 2) For measuring PI3K | |
| Dynabeads Protein G (Life technologies) | 22.5 mg/mL |
| anti-PI3K 110α antibody (IgG) (Santa Cruz Biotechnology) | 60 μg/mL |

Third Reagent

| | |
|---|---|
| 1) For measuring MEK | |
| Tris-HCl pH 7.5 (SIGMA) | 100 mM |
| NaCl (Wako Pure Chemical Industries, Ltd.) | 300 mM |
| unactive-ERK (Signalchem) | 100 μg/mL |
| Adenosine triphosphate (ATP, SIGMA) | 10 mM |
| 2) For measuring PI3K | |
| Tris-HCl pH 7.5 (SIGMA) | 100 mM |
| NaCl (Wako Pure Chemical Industries, Ltd.) | 300 mM |
| L-a-Phosphatidylinositol sodium salt (Signalchem) | 0.5 mM |
| Adenosine triphosphate (ATP, SIGMA) | 10 mM |

Fourth Reagent

| | |
|---|---|
| Tris-HCl pH 8.5 (SIGMA) | 100 mM |
| Magnesium sulfate heptahydrate (Wako Pure Chemical Industries, Ltd.) | 10 mM |
| D-Glucose (Wako Pure Chemical Industries, Ltd.) | 40 mM |
| ADP-Hexokinase (Asahi Kasei Corp.) | 20 KU/L |
| Glucose-6-phosphate dehydrogenase (Roche Diagnostics K.K.) | 20 KU/L |
| Diphorase (Asahi Kasei Corp.) | 5 KU/L |
| NADP (Roche Diagnostics K.K.) | 3 mM |

Fifth Reagent

| | |
|---|---|
| Sodium Carbonate pH 9.8 (Wako Pure Chemical Industries, Ltd.) | 100 mM |
| Luminol (Wako Pure Chemical Industries, Ltd.) | 1 mM |
| P-indophenol (Wako Pure Chemical Industries, Ltd.) (photosensitizer) | 0.3 mM |
| Peroxidase (TOYOBO CO., LTD.) | 20 KU/L |

Sixth Reagent

| | |
|---|---|
| Tris-HCl pH 7.5 (SIGMA) | 100 mM |
| NaCl (Wako Pure Chemical Industries, Ltd.) | 300 mM |
| Polyoxyethylene sorbitan monolaurate (NACALAI TESQUE, INC.) | 0.05% |

Preparation of a Cell Lysate for Kinase Activity

A lysate of established cells used for kinase analysis was prepared as follows. Cells were cultured in a medium with 10% FBS (fetal bovine serum) suitable for each cell. Cells were collected after culturing up to about $1\times10^7$ cells, and washed once with PBS. Next, cells were lysed by adding 0.5 mL of first reagent and stirring with a vortex mixer. In order to remove non-lysed material, centrifugation was carried out at 15000 rpm for 5 minutes to obtain a cell lysate.

Capture and a Kinase Reaction of MEK in a Cell Lysate

To 0.2 mL of cell lysate, 0.2 mL of second reagent for measuring MEK was added, and the obtained mixture was stirred at 4° C. for 2 hours to selectively precipitate MEK molecules. After completion of the reaction, the supernatant was removed and 0.5 mL of sixth reagent was then added, and a washing operation by suspending MEK capturing magnetic particles was carried out three times. After washing, 0.5 mL of third reagent for measuring MEK was added, and a kinase reaction was carried out at 37° C. for 2 hours with shaking. After completion of the reaction, the reaction liquid was collected and activity was measured by an HPLC method and a chemiluminescent method. The method for measuring activity by an HPLC method is the same as in Example 2.

Activity Measurement of MEK Using a Chemiluminescent Method

MEK activity was measured by indirectly measuring ADP generated by the kinase reaction, specifically by combining known enzyme reactions (see diagram below).

[Chemical Formula 3]

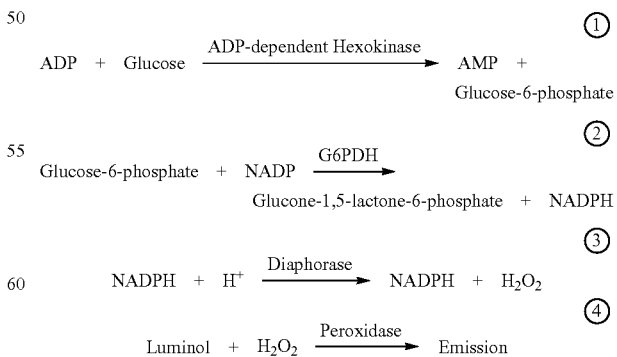

First, the above three stages of enzyme reaction were carried out to convert ADP into hydrogen peroxide. Specific enzyme reactions are 1) the generation of Glucose-6-phosphate from ADP and Glucose by ADP-dependent Hexokinase, 2) the generation of NADPH from Glucose-6-phosphate and NADP by Glucose-6-phosphate dehydrogenase (G6PDH), and 3) the generation of hydrogen peroxide from NADPH and hydrogen ion by Diaphorase. Furthermore, 4) hydrogen peroxide was allowed to react with Luminol and Peroxidase to emit light, which was detected by a detector. The detected intensity of chemiluminescence was converted into kinase activity via ADP concentration.

As a specific measurement protocol, a reaction liquid obtained in the above kinase reaction was 4-fold diluted with Milli-Q to obtain a solution, which was applied to a 96 well plate at 20 μL, and 20 μL of fourth reagent was added thereto. The plate was incubated at 37° C. for 10 minutes with shaking to generate hydrogen peroxide dependent on the amount of ADP. After completion of the reaction, the plate was set to a luminometer (manufactured by Thermo Fisher Scientific) dealing with plate measurement, and 30 μL of fifth reagent was added to each well. The intensity of chemiluminescence generated by adding the reagent was measured. The measured intensity of chemiluminescence was converted into kinase activity via ADP concentration.

It should be noted that the concentration of ADP was calculated using a calibration curve created in advance using ADP with a known concentration. In addition, 1 unit (U) was prescribed as an enzyme level for 1 pmol ADP generated at 37° C. for a minute.

Capture of PI3K and a Kinase Reaction in a Cell Lysate

As is the case with MEK, to 0.2 mL of cell lysate, 0.2 mL of second reagent for measuring PI3K was added, and the obtained mixture was stirred at 4° C. for 2 hours to selectively precipitate PI3K molecules. After completion of the reaction, the supernatant was removed and 0.5 mL of sixth reagent was then added, and a washing operation by suspending PI3K capturing magnetic particles was carried out three times. After washing, 0.5 mL of third reagent for measuring PI3K was added, and a kinase reaction was carried out at 37° C. for 2 hours with shaking. After completion of the reaction, the reaction liquid was collected and activity was measured by an HPLC method and a chemiluminescent method. The method for measuring activity by an HPLC method is the same as in Example 2.

Activity Measurement of PI3K Using a Chemiluminescent Method

As is the case in the activity measurement of MEK, PI3K activity was also measured by indirectly measuring ADP generated by the kinase reaction, specifically by combining known enzyme reactions (see diagram below).

[Chemical Formula 4]

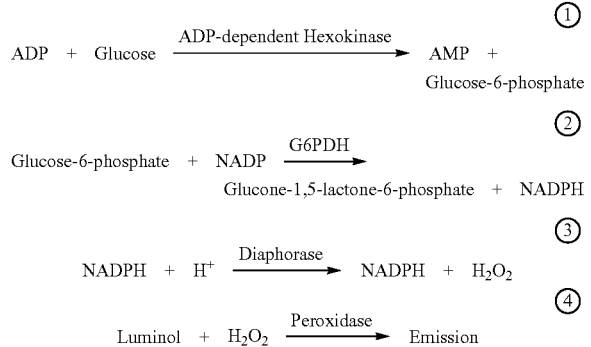

First, the above three stages of enzyme reaction were carried out to convert ADP into hydrogen peroxide. Specific enzyme reactions are 1) the generation of Glucose-6-phosphate from ADP and Glucose by ADP-dependent Hexokinase, 2) the generation of NADPH from Glucose-6-phosphate and NADP by Glucose-6-phosphate dehydrogenase (G6PDH), and 3) the generation of hydrogen peroxide from NADPH and hydrogen ion by Diaphorase. Furthermore, 4) hydrogen peroxide was allowed to react with Luminol and Peroxidase to emit light, which was detected by a detector. The detected intensity of chemiluminescence was converted into kinase activity via ADP concentration.

2. Results

Correlation with an HPLC method in the activity measurement of MEK is shown in FIG. 30.

Correlation was confirmed using an HPLC method as X as and the present method as Y. As shown in FIG. 30, good results were obtained, in which Y=1.2168X−0.2884 and the correlation coefficient was 0.896. Because of this, it can be said that the present method can accurately measure MEK activity in human breast cancer cells.

Similarly, correlation with an HPLC method in the activity measurement of PI3K is shown in FIG. 31.

Correlation was confirmed using an HPLC method as X and the present method as Y. As shown in FIG. 31, good results were obtained, in which Y=0.9027X−0.0337 and the correlation coefficient was 0.943. Because of this, it can be said that the present method can accurately measure PI3K activity in human breast cancer cells.

Example 8

Activity Measurement of Kinases in a Tumor Resected from a Tumor-Bearing Mice Prepared from Cultured Cells 1. Method A cultured triple negative breast cancer cell line was injected under the skin of nude mice to prepare tumor-bearing mice, and a tumor tissue was established and then removed at the time of a predetermined size. A lysate including a target kinase was prepared from the removed tumor, the target kinase was supplemented using an antibody specific to each kinase, and the measurement was then carried out using a chemiluminescent method. The method for preparing a measurement sample and the measurement method will be described below. It should be noted that the measurement method, reagent names, etc. are the same as in the "activity measurement of kinases in a cultured cell extract by a kit for the activity measurement of kinases having a chemiluminescent method as a measurement principle" in Example 7.

Preparation of a Cell Suspension and Tumor-Bearing Mice

The cell lines of MDA-MB-231 classified as MA, HCC70 classified as S and SUM185PE classified as PA were cultured by the above-described method, and after release with trypsin, the cells was suspended with Matrigel basement membrane matrix (manufactured by Corning Incorporated) to about 7×10⁶ cells/mL to prepare a cell suspension. Using a 27 gauge syringe, 0.1 mL of cell suspension was injected under the skin of 5-week old female nude mice (manufactured by CLEA Japan, Inc.) to create cancer-bearing mice, and tumor volumes were observed. The tumor volume was calculated by major axis×(minor axis)²/2.

Resection of a Tumor

A tumor was resected at a stage when a tumor volume reached 300 mm³. For an analysis, a tumor created using MDA-MB-231, a tumor created using HCC70, and a tumor created using SUM185PE were defined as tumor 1, tumor 2 and tumor 3, respectively.

Preparation of a Tumor Lysate for Kinase Activity

A lysate of a tumor used for kinase analysis was prepared as follows. The weight of a resected tumor was measured, and 16 mL of first reagent per g of tumor was added. The tumor was ground using a muddler and a mortar under ice cooling to break a tumor tissue. In order to remove non-lysed material, centrifugation was carried out at 15000 rpm for 5 minutes to obtain a tumor lysate.

Capture and a Kinase Reaction of MEK in a Tumor Lysate
Activity Measurement of MEK Using a Chemiluminescent Method
Capture and a Kinase Reaction of PI3K in a Tumor Lysate
Activity Measurement of PI3K Using a Chemiluminescent Method These are the same as in the "activity measurement of kinases in a cultured cell extract by a kit for the activity measurement of kinases having a chemiluminescent method as a measurement principle" in Example 7.

2. Results

The results of activity measurement of tumors derived from three types of cell line are shown in FIG. 32 (the number of individuals N=3). Samples were prepared from tumors derived from a cell line sensitive to an MEK inhibitor (MA) and a cell line sensitive to a PI3K inhibitor (PA), and "PI3K activity/MEK activity" was calculated. In this case, when a tumor sample derived from HCC70 cells not corresponding to both MA and PA, for example, is a reference standard, it can be suggested that a tumor having a lower "PI3K activity/MEK activity" than that of the reference standard is sensitive to an MEK inhibitor, and a tumor having a higher "PI3K activity/MEK activity" than that of the reference standard is sensitive to a PI3K inhibitor. Table 10 shows the p value of the "PI3K activity/MEK activity" of a cell line sensitive to an MEK inhibitor (MA) or a cell line sensitive to a PI3K inhibitor (PA) with reference to the reference standard.

TABLE 10

|  | MDA-MB-231 | SUM185PE |
|---|---|---|
| HCC70 | <0.05 | <0.05 |

Example 9

Test of Suppressing Tumor Growth by Drug Administration Using Tumor-Bearing Mice Prepared from Cultured Cells 1. Method A cultured triple negative breast cancer cell line was injected under the skin of nude mice to create cancer-bearing mice, and a tumor tissue was established and a PI3K inhibitor and an MEK inhibitor were then administered. Tumor volumes were measured to observe an anti-tumor effect. The method for preparing a tumor-bearing mice and the administration route are as follows.

Preparation of a Cell Suspension and Tumor-Bearing Mice

The cell lines of MDA-MB-231, HCC70 and SUM185PE were cultured by the above-described method, and after release with trypsin, the cells was suspended with Matrigel basement membrane matrix (manufactured by Corning Incorporated) to about 7×10$^6$ cells/mL to prepare a cell suspension. Using a 27 gauge syringe, 0.1 mL of cell suspension was injected under the skin of 5-week old female nude mice (manufactured by CLEA Japan, Inc.) to prepare tumor-bearing mice.

Preparation of a Drug Solution

Trametinib, an MEK inhibitor, and wortmannin, a PI3K inhibitor, were each dissolved in PBS with 1% dimethyl-sulfoxide (DMSO) to 0.3 mg/kg to obtain a drug solution. In addition, PBS with 1% DMSO was used as a control.

Administration Route and Experiment Design

Individuals whose tumor volume reached 300 mm$^3$ were randomly divided into 3 groups and administration was initiated. As an administration route, a drug solution was orally administered once-daily for 14 days and the tumor volume was observed. The tumor volume was calculated by major axis×(minor axis)$^2$/2.

2. Results

FIGS. 33 to 35 show the results of the test of suppressing tumor growth by each inhibitor using the number of individuals N=6 in each group (Control group, Trametinib-administered group and Wortmannin-administered group) (FIG. 33: MDA-MB-231 derived tumor-bearing mice, FIG. 34: HCC70 dericed tumor-bearing mice, and FIG. 35: SUM185PE derived tumor-bearing mice). In addition, Table 11 shows the results of p values calculated by a significance test about tumor volumes between each group and the control group at 15th day, the next day of drug administration for 14 days. Mann-Whitney U test was used as the test method.

TABLE 11

|  | MDA-MB-231 | HCC70 | SUM185PE |
|---|---|---|---|
| TRAMETINIB GROUP | <0.005 | <0.005 | 0.9372 |
| WORTMANNIN GROUP | 0.0656 | <0.05 | <0.05 |

The growth of a tumor derived from MDA-MB-231, a cell line sensitive to an MEK inhibitor (MA) in which the "PI3K activity/MEK activity" showed a low value in Example 7, was significantly suppressed by administering trametinib, an MEK inhibitor, while a significant suppressive effect was not obtained by administering wortmannin, a PI3K inhibitor.

The growth of a tumor derived from SUM185PE, a cell line sensitive to a PI3K inhibitor (PA) in which the "PI3K activity/MEK activity" showed a high value in Example 7, was significantly suppressed by administering wortmannin, a PI3K inhibitor, while a significant growth suppressive effect was not obtained by administering trametinib, an MEK inhibitor.

About the growth of a tumor derived from HCC70, a cell line sensitive to both inhibitors (S) in which the "PI3K activity/MEK activity" showed an intermediate value in Example 7, a significant growth suppressive effect was observed by administering wortmannin, a PI3K inhibitor, and administering trametinib, an MEK inhibitor, but the effects varied depending on drugs.

From the above results, it was suggested that the measurement of the PI3K activity/MEK activity ratio of cancer tissue cells isolated from a cancer patient was an extremely effective guideline to select a drug suitable for the cancer treatment of the cancer patient, and an effective treatment was possible by preferentially administering a selected drug. That is, a therapy regimen in which an MEK inhibitor is preferentially administered when the "PI3K activity/MEK activity" shows a low value and a PI3K inhibitor is preferentially administered when the "PI3K activity/MEK activity" shows a high value is established, and thus "PI3K activity/MEK activity" can be used as a predictive factor for an effect of chemotherapy to cancers.

In particular, a novel therapy can be also provided to patients diagnosed as triple negative breast cancer (TNBC). Patients diagnosed as TNBC have conventionally selected a radiation therapy or chemotherapy using an anticancer drug as a therapy regimen after the extirpative surgery of a tumor tissue. At this time, the method involved in the invention of the application can provide one of guidelines (predictive factor) to select an anticancer drug which should be used.

INDUSTRIAL APPLICABILITY

A novel method for classifying cancer cells into subtypes by an analysis method using the activity measurement of two types of protein kinase, and a method for determining the drug resistance of cancer cells based on the subtype classification method contribute to determining a drug effect on a living body based on the activity measurement of protein kinases in cells derived from the living body. Such method can be applied for example to determine, using cancer tissue cells isolated from a cancer patient, the drug sensitivity of the cancer cells, and to use the results for the drug therapy of the cancer patient.

An anticancer drug therapy itself has a great burden to patients, and it is important to decide a therapy regimen suitable for a patient before the initiation of treatment in order to maintain quality of life (QOL) of the patient. The invention of the application can be applied for not only a therapy regimen for chemical treatment before a surgical operation (preoperative anticancer drug treatment) but also a therapy regimen after tumor resection by a surgical operation.

The invention claimed is:

1. A method for distinguishing cancer cells, which method distinguishes
   1) cancer cells sensitive to a PI3K inhibitor and insensitive to an MEK inhibitor, and/or cancer cells sensitive to an MEK inhibitor and insensitive to a PI3K inhibitor, from
   2) cancer cells insensitive to both a PI3K inhibitor and an MEK inhibitor, and/or sensitive to both a PI3K inhibitor and an MEK inhibitor;
   the method being characterized by distinguishing cancer cells by the enzyme activity ratio of PI3K and MEK in cancer cells,
   wherein the enzyme activity is measured by at least one of:
   capturing the enzyme using an antibody which specifically binds to PI3K or MEK; and
   using a substrate specific to PI3K and/or MEK.

2. The method according to claim 1, wherein the method further distinguishes cancer cells by normalization using the total amount of protein.

3. The method according to claim 1, wherein the method further distinguishes cancer cells by normalization using the activity value of lactate dehydrogenase (LDH).

4. The method according to claim 1, in which the enzyme activity is carried out by measuring the amount of ADP generated.

5. The method according to claim 1, which is used to determine the effect prediction of a PI3K inhibitor or an MEK inhibitor.

6. The method according to claim 1, wherein the PI3K inhibitor is wortmannin.

7. The method according to claim 1, wherein the MEK inhibitor is trametinib.

8. The method according to claim 1, wherein cancer cells are a tissue sample.

9. The method according to claim 8, wherein the tissue sample is a biopsy tissue sample.

10. The method according to claim 9, wherein the biopsy tissue sample is derived from a patient with triple negative breast cancer.

11. A kit used for a method according to claim 1, the kit comprising an anti-PI3K antibody and an anti-MEK antibody.

12. The kit of claim 11, wherein the kit is for measuring the PI3K activity and MEK activity, the kit comprising
   1) a first reagent for cytolysis, comprising a surface active agent, a protease inhibitor, and a phosphatase inhibitor,
   2A) a second reagent for measuring MEK, comprising the anti-MEK antibody,
   2B) a second reagent for measuring PI3K, comprising the anti-PI3K antibody,
   3A) a third reagent for measuring MEK, comprising a substrate for MEK and ATP,
   3B) a third reagent for measuring PI3K, comprising a substrate for PI3K and ATP,
   4) a fourth reagent comprising D-Glucose; ADP-Hexokinase; Glucose-6-phosphate dehydrogenase; Diaphorase and NADP,
   5) a fifth reagent comprising Luminol and Peroxidase, and
   6) a washing sixth reagent comprising a surface active agent.

* * * * *